(12) United States Patent
Kim

(10) Patent No.: US 9,504,372 B2
(45) Date of Patent: Nov. 29, 2016

(54) INTRADURAL ENDOSCOPE

(76) Inventor: Daniel H. Kim, Houston, TX (US)

( * ) Notice: Subject to any disclaimer, the term of this patent is extended or adjusted under 35 U.S.C. 154(b) by 86 days.

(21) Appl. No.: 13/509,571

(22) PCT Filed: Nov. 12, 2010

(86) PCT No.: PCT/US2010/056609
§ 371 (c)(1),
(2), (4) Date: Aug. 3, 2012

(87) PCT Pub. No.: WO2011/060317
PCT Pub. Date: May 19, 2011

(65) Prior Publication Data
US 2012/0296166 A1  Nov. 22, 2012

Related U.S. Application Data

(60) Provisional application No. 61/261,136, filed on Nov. 13, 2009, provisional application No. 61/319,664, filed on Mar. 31, 2010.

(51) Int. Cl.
| | | |
|---|---|---|
| *A61B 1/00* | (2006.01) | |
| *A61B 1/04* | (2006.01) | |
| *A61M 31/00* | (2006.01) | |
| *A61M 37/00* | (2006.01) | |
| *A61M 25/00* | (2006.01) | |
| *A61B 1/005* | (2006.01) | |
| *A61B 1/018* | (2006.01) | |
| *A61B 17/34* | (2006.01) | |

(52) U.S. Cl.
CPC ............... *A61B 1/04* (2013.01); *A61B 1/0051* (2013.01); *A61B 1/018* (2013.01); *A61B 17/3401* (2013.01)

(58) Field of Classification Search
USPC ........ 600/104, 106, 107, 114–116, 239–152; 604/506, 95.01–95.05, 528; 606/1
See application file for complete search history.

(56) References Cited

U.S. PATENT DOCUMENTS

| | | |
|---|---|---|
| 5,085,631 A | 2/1992 | Leighton |
| 5,119,832 A | 6/1992 | Xavier |
| 5,354,266 A | 10/1994 | Snoke |
| 5,395,342 A | 3/1995 | Yoon |
| 5,396,880 A | 3/1995 | Kagan et al. |
| 5,419,312 A * | 5/1995 | Arenberg ........... A61B 1/00165 600/108 |
| 5,470,318 A | 11/1995 | Griffith, III et al. |
| 5,505,686 A | 4/1996 | Willis et al. |
| 5,738,650 A | 4/1998 | Gregg |
| 5,868,665 A | 2/1999 | Biggs |
| 6,464,682 B1 | 10/2002 | Snoke |

(Continued)

FOREIGN PATENT DOCUMENTS

JP    11197100 A  *  7/1999  ............... A61B 1/00

OTHER PUBLICATIONS

International search report for application No. PCT/US2010/056609 dated May 30, 2011.

(Continued)

*Primary Examiner* — Ryan Henderson
(74) *Attorney, Agent, or Firm* — Patterson & Sheridan, LLP

(57) ABSTRACT

A method for treating a patient includes inserting an endoscope into an intradural space of the patient via an interspace of a vertebral column of the patient; steering the endoscope along the intradural space to a location; and performing a medical procedure at the location using a working lumen of the endoscope.

15 Claims, 24 Drawing Sheets

(56) References Cited

U.S. PATENT DOCUMENTS

| | | | |
|---|---|---|---|
| 6,470,209 B2 | 10/2002 | Snoke | |
| 6,984,203 B2 | 1/2006 | Tartaglia et al. | |
| 7,011,647 B2 | 3/2006 | Purdy et al. | |
| 7,150,737 B2 | 12/2006 | Purdy et al. | |
| 2003/0014016 A1* | 1/2003 | Purdy | 604/174 |
| 2003/0069475 A1* | 4/2003 | Banik | A61B 1/00016 600/152 |
| 2003/0093105 A1 | 5/2003 | Huffmaster | |
| 2004/0143160 A1 | 7/2004 | Couvillon | |
| 2004/0249267 A1 | 12/2004 | Gilboa | |
| 2005/0085790 A1* | 4/2005 | Guest et al. | 604/506 |
| 2006/0111754 A1* | 5/2006 | Rezai et al. | 607/41 |
| 2006/0184098 A1 | 8/2006 | Barnitz et al. | |
| 2006/0224101 A1 | 10/2006 | Glenn | |
| 2007/0038224 A1 | 2/2007 | Ortiz | |
| 2007/0185384 A1 | 8/2007 | Bayer et al. | |
| 2007/0239138 A1* | 10/2007 | Lawrence et al. | 604/531 |
| 2009/0028670 A1* | 1/2009 | Garcia et al. | 414/7 |
| 2009/0030380 A1 | 1/2009 | Binmoeller | |
| 2009/0062871 A1* | 3/2009 | Chin et al. | 606/86 R |
| 2009/0076357 A1 | 3/2009 | Purdy | |
| 2009/0143645 A1 | 6/2009 | Matthes | |
| 2009/0259141 A1 | 10/2009 | Ewers et al. | |
| 2010/0016666 A1 | 1/2010 | Hasegawa | |

OTHER PUBLICATIONS

Zaaroor, M.—Morphological study of the spinal canal content for subarachnoid endoscopy, Minim Invasive Neurosurg, Aug. 1, 2006, PubMed, http://www.ncbi.nlm,nih.gov/pubmed/17041833.

* cited by examiner

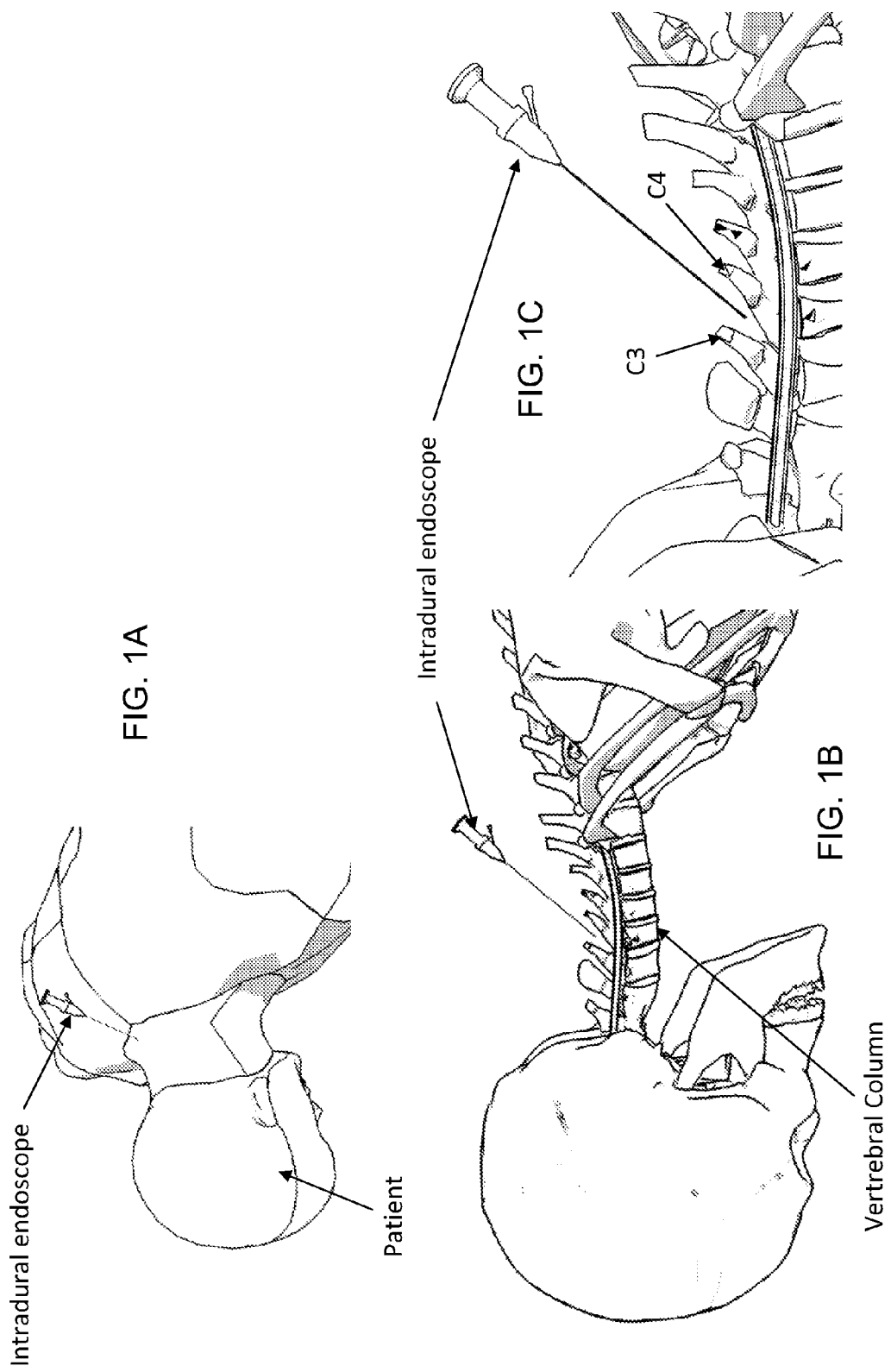

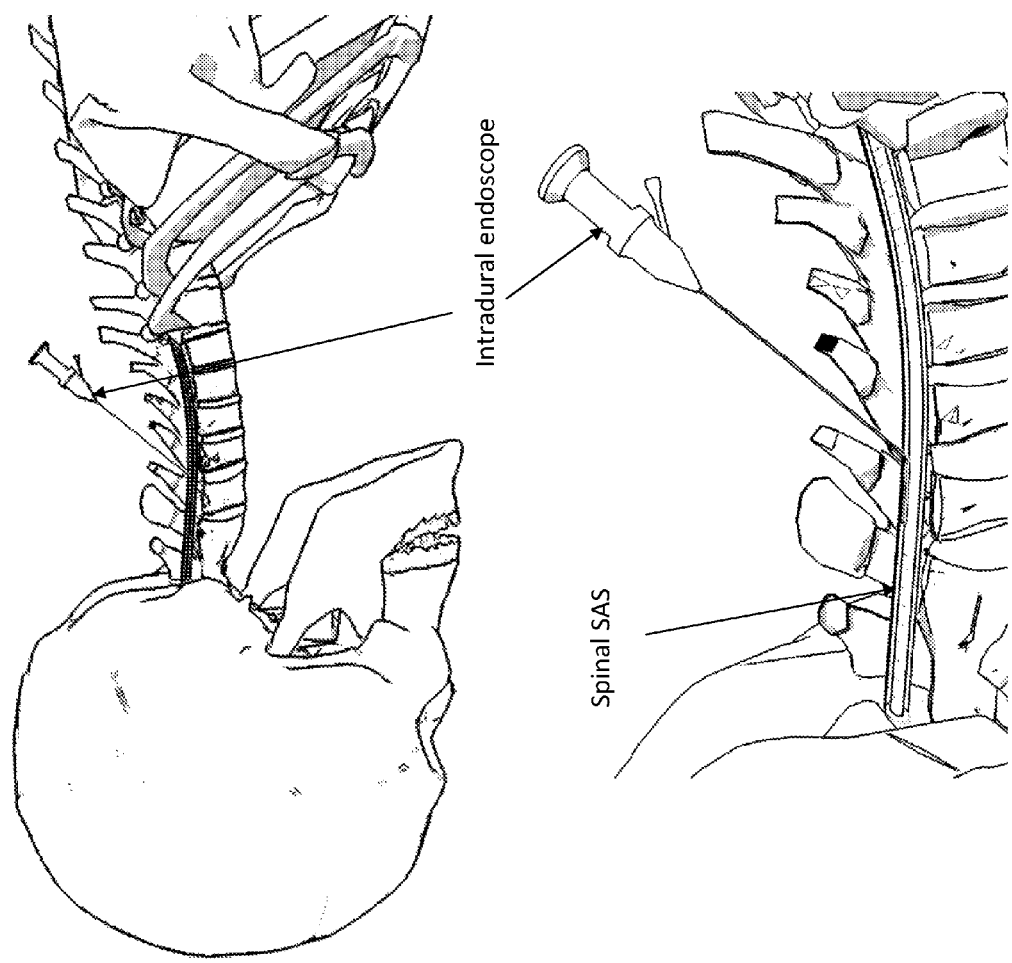

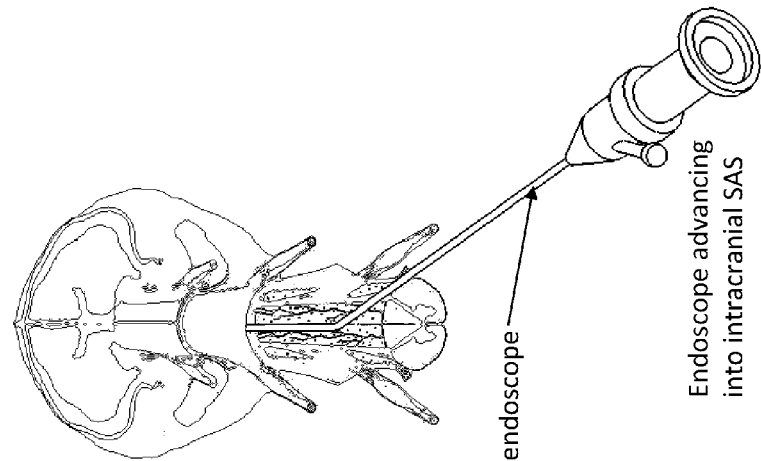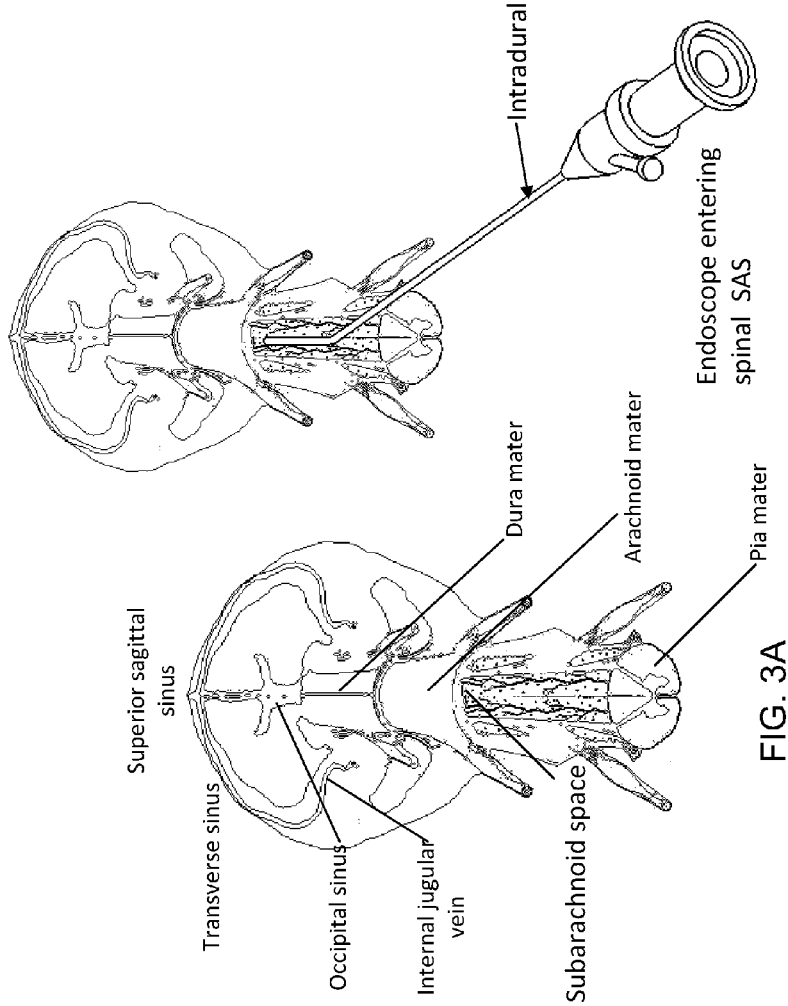

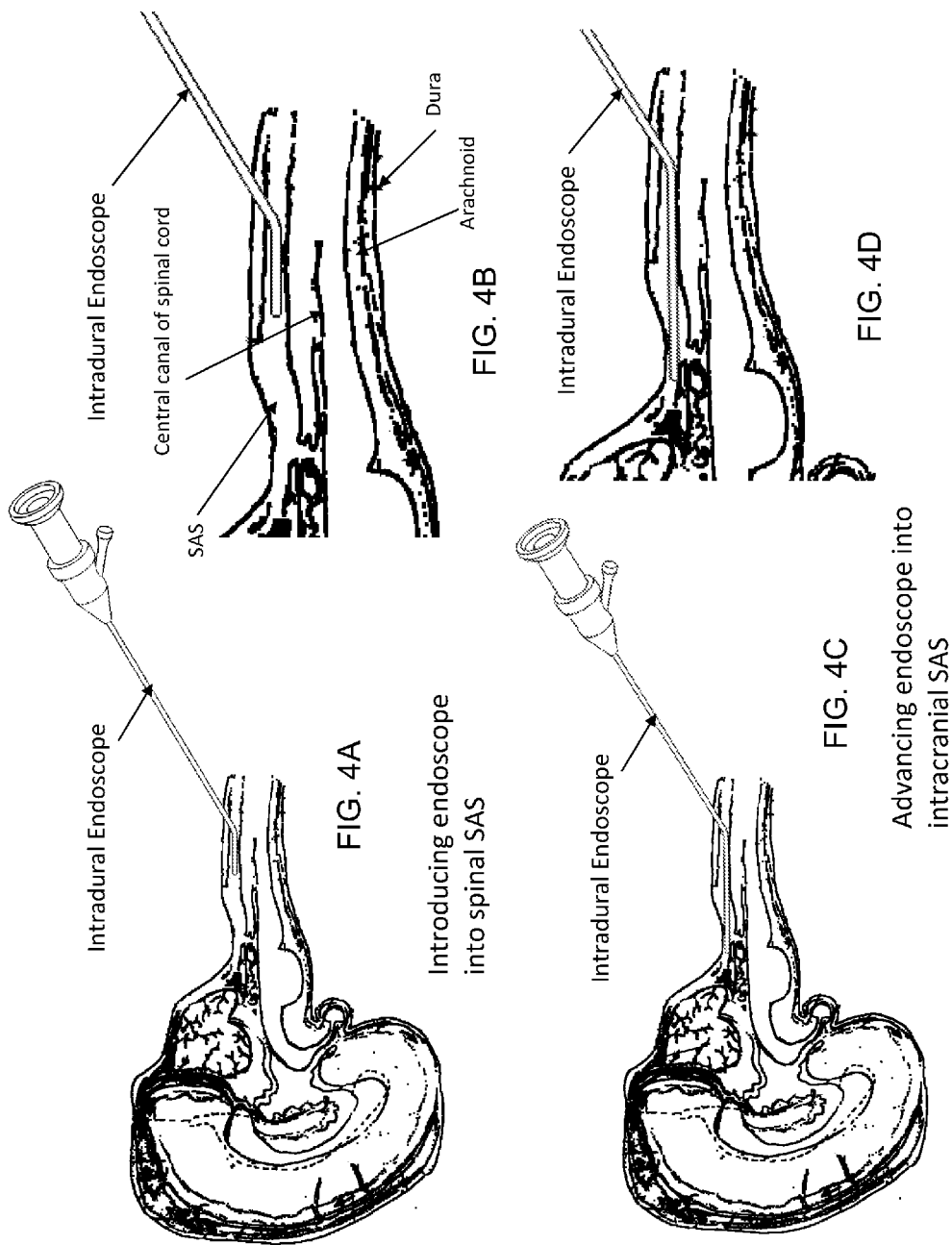

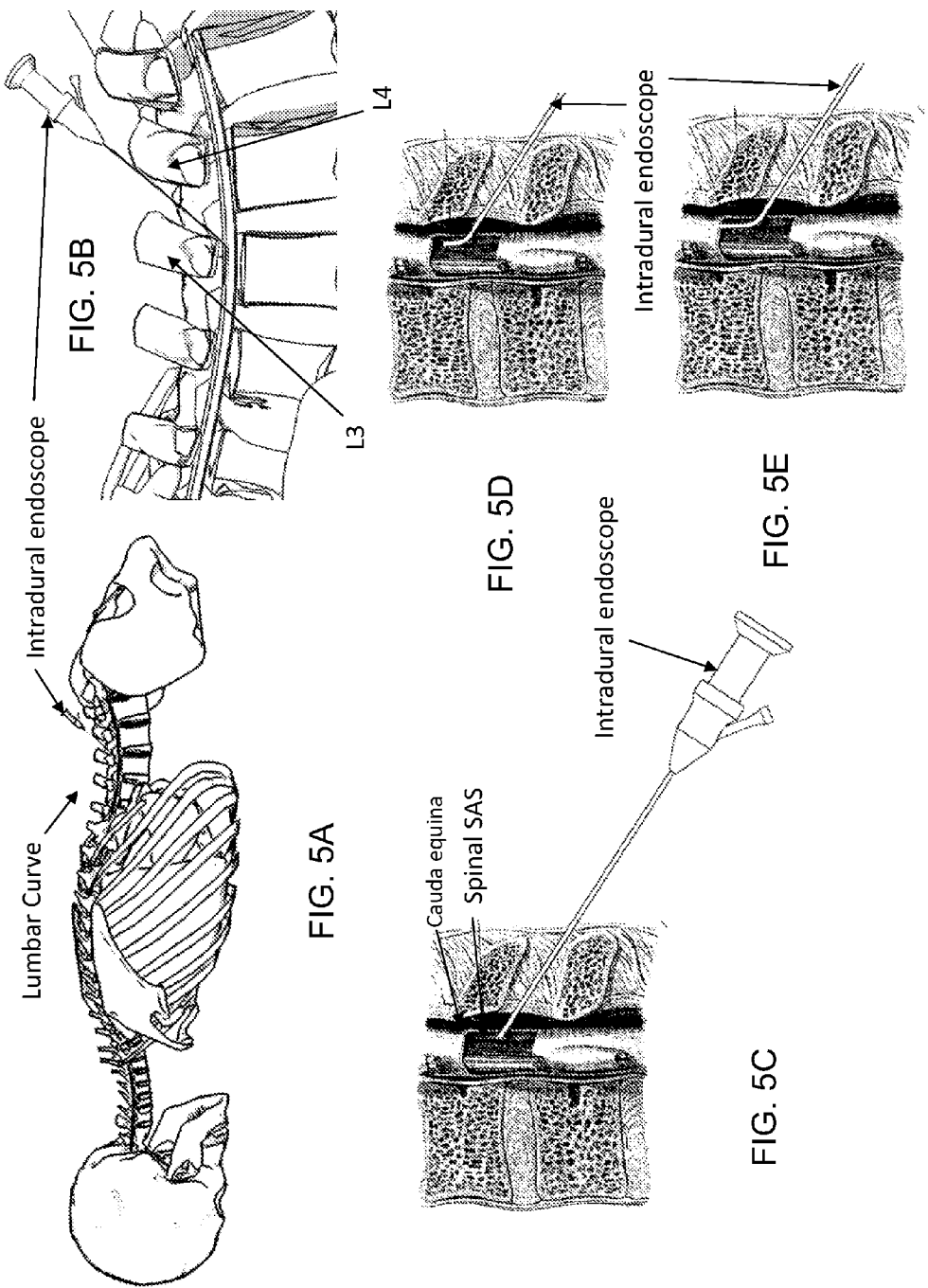

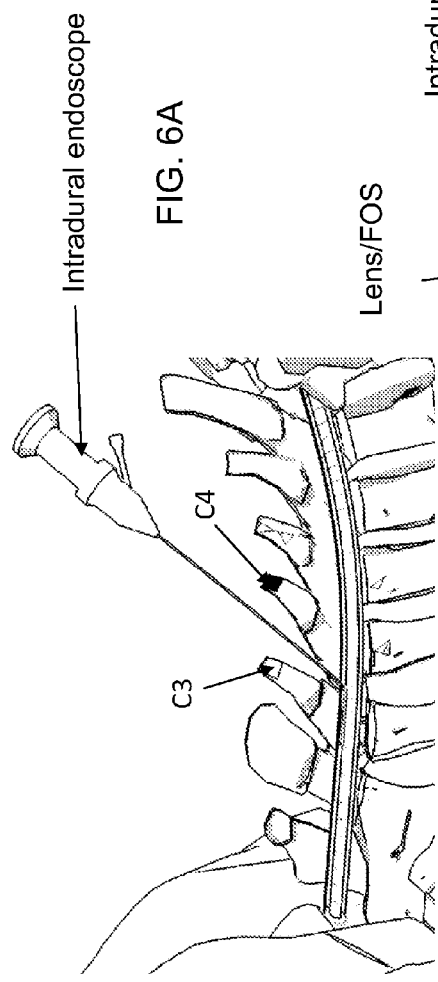
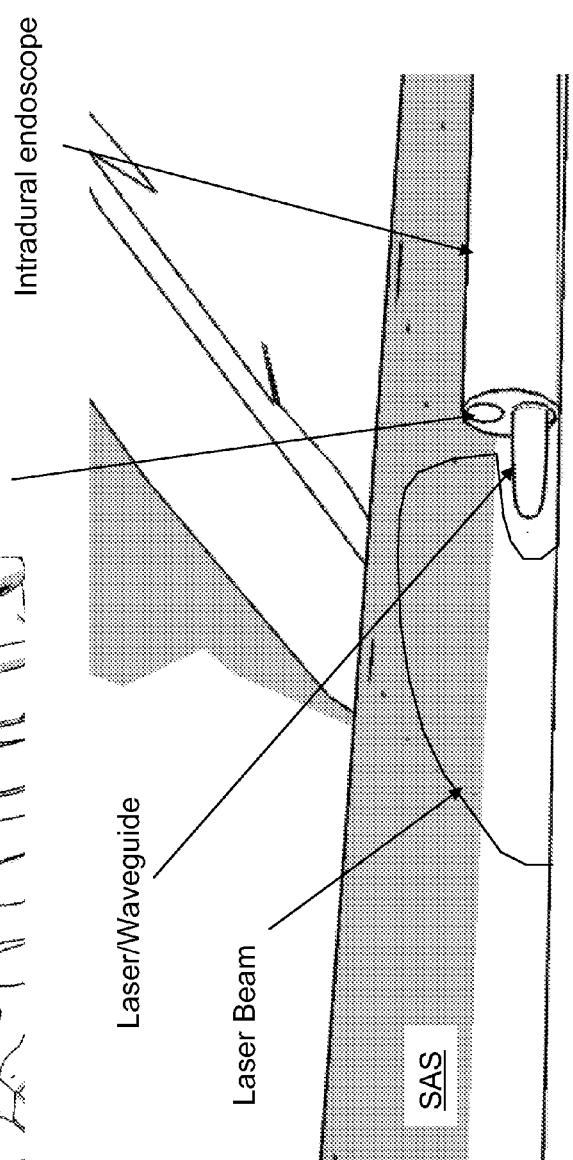
FIG. 6A
FIG. 6B

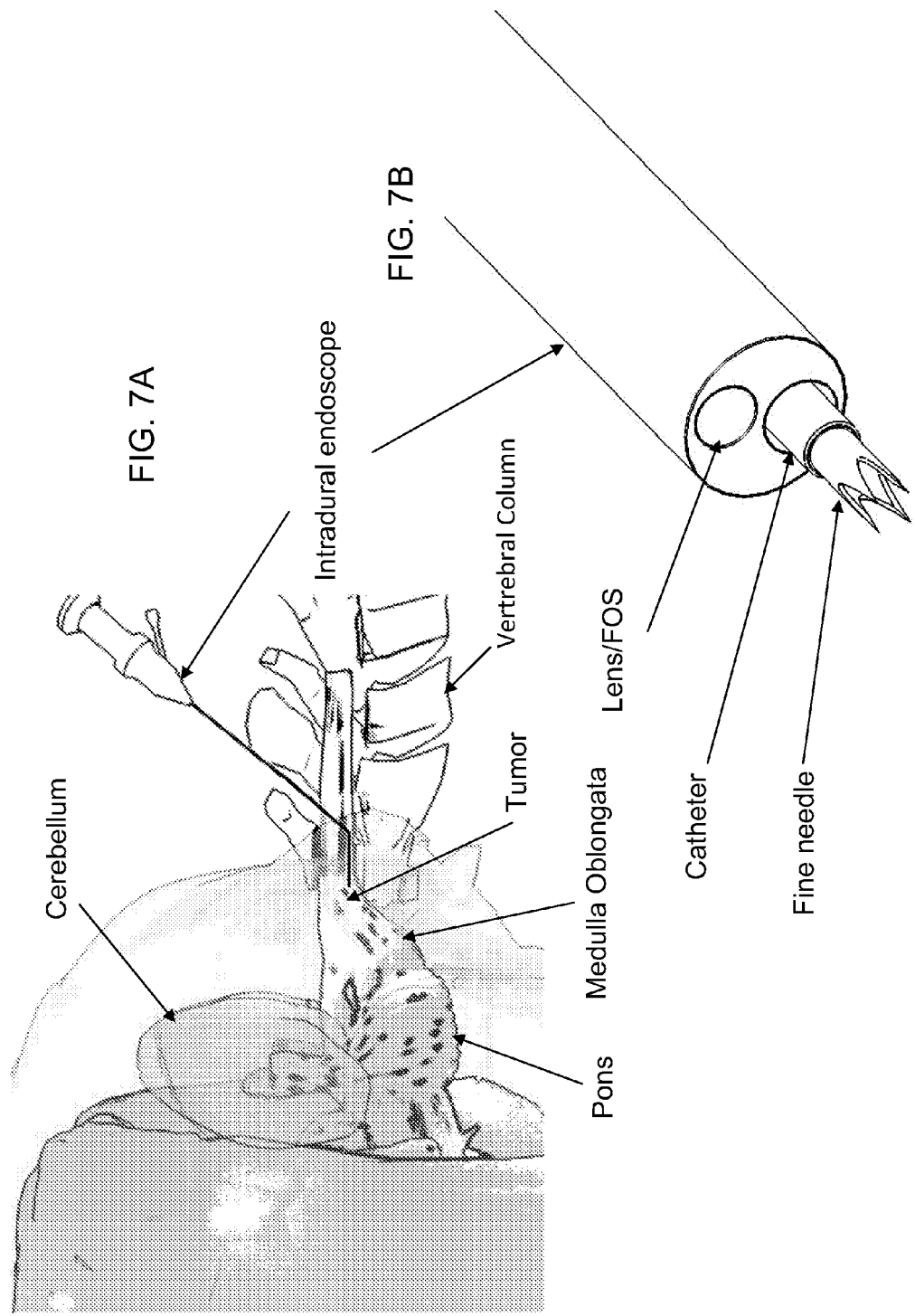

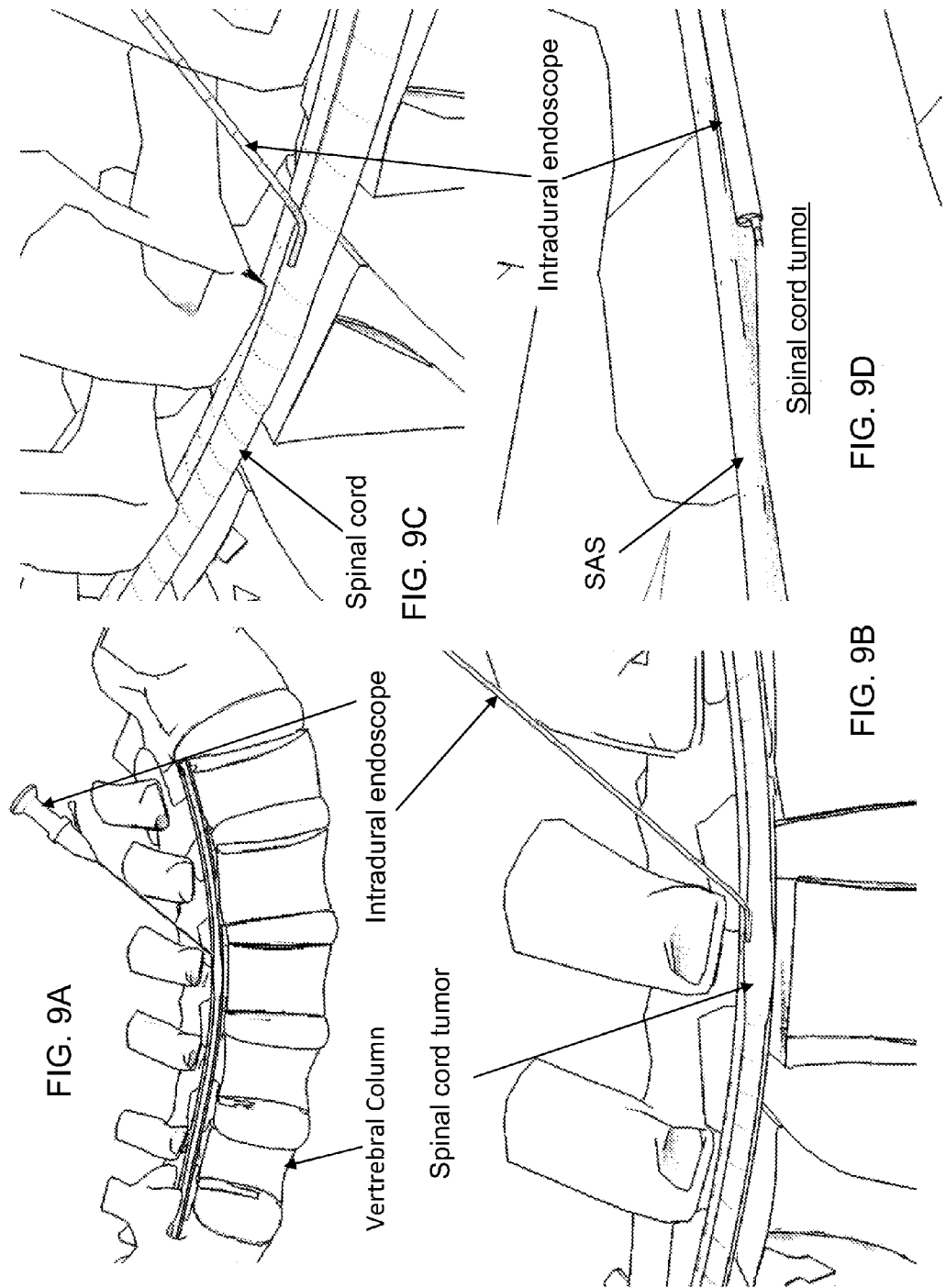

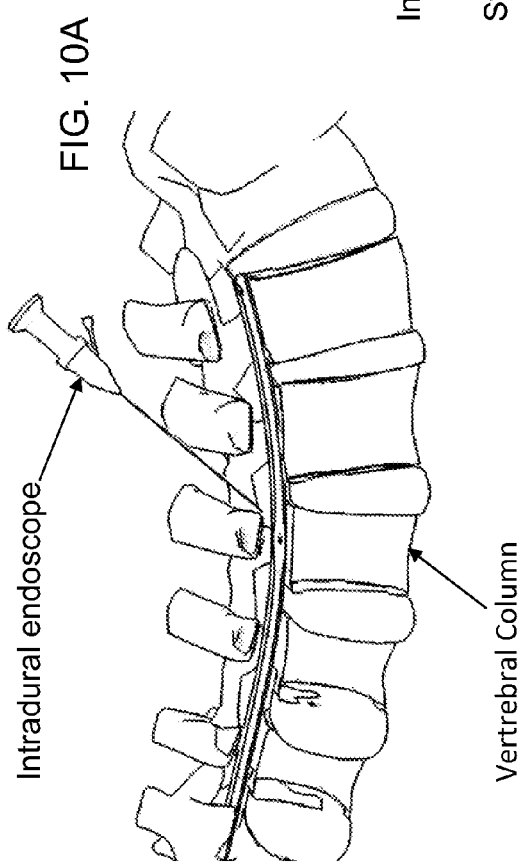
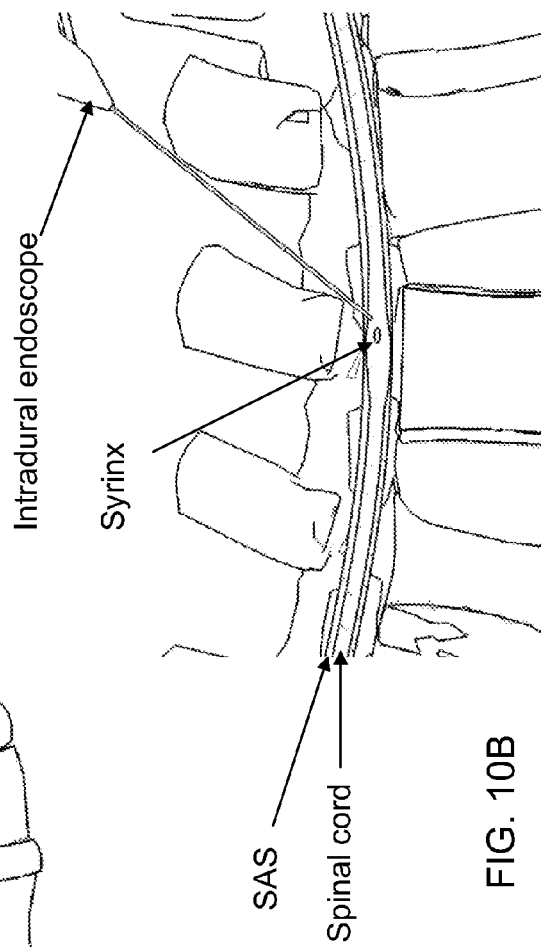
FIG. 10A
FIG. 10B

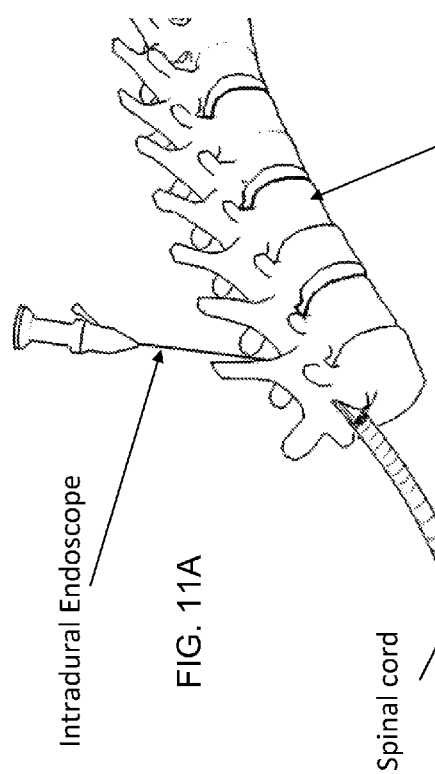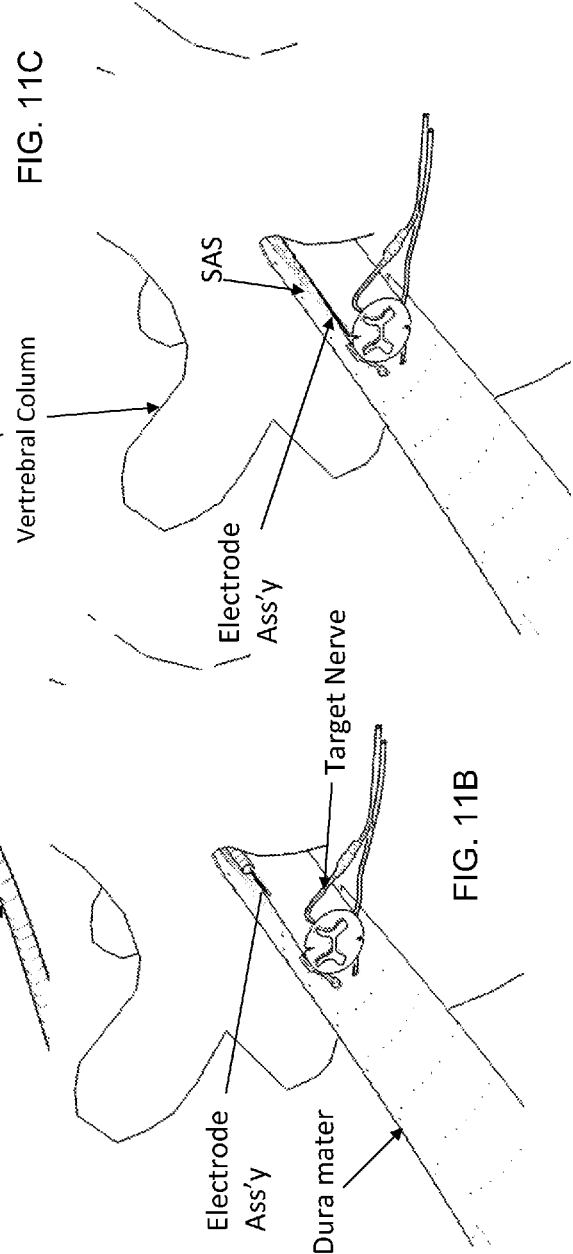

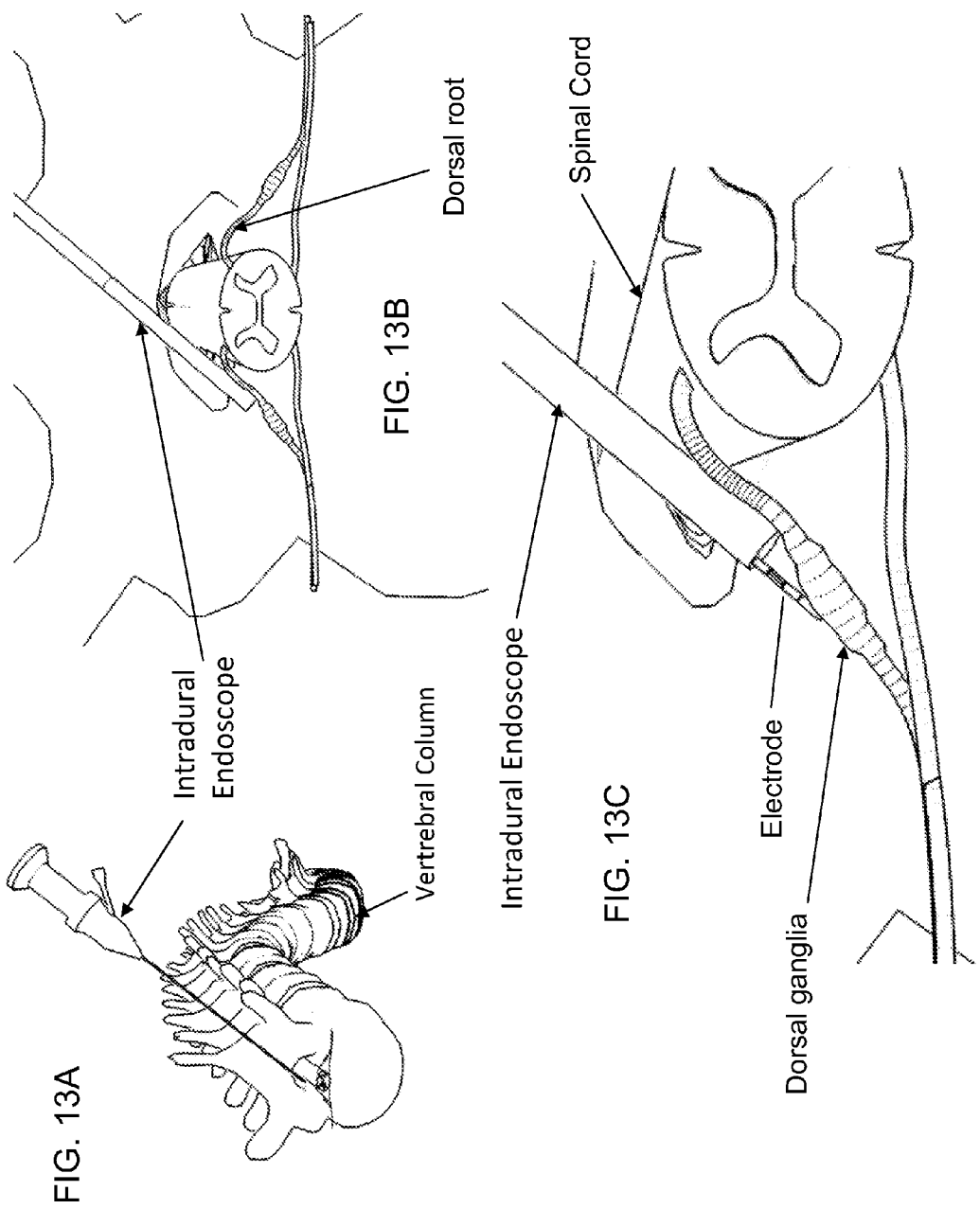

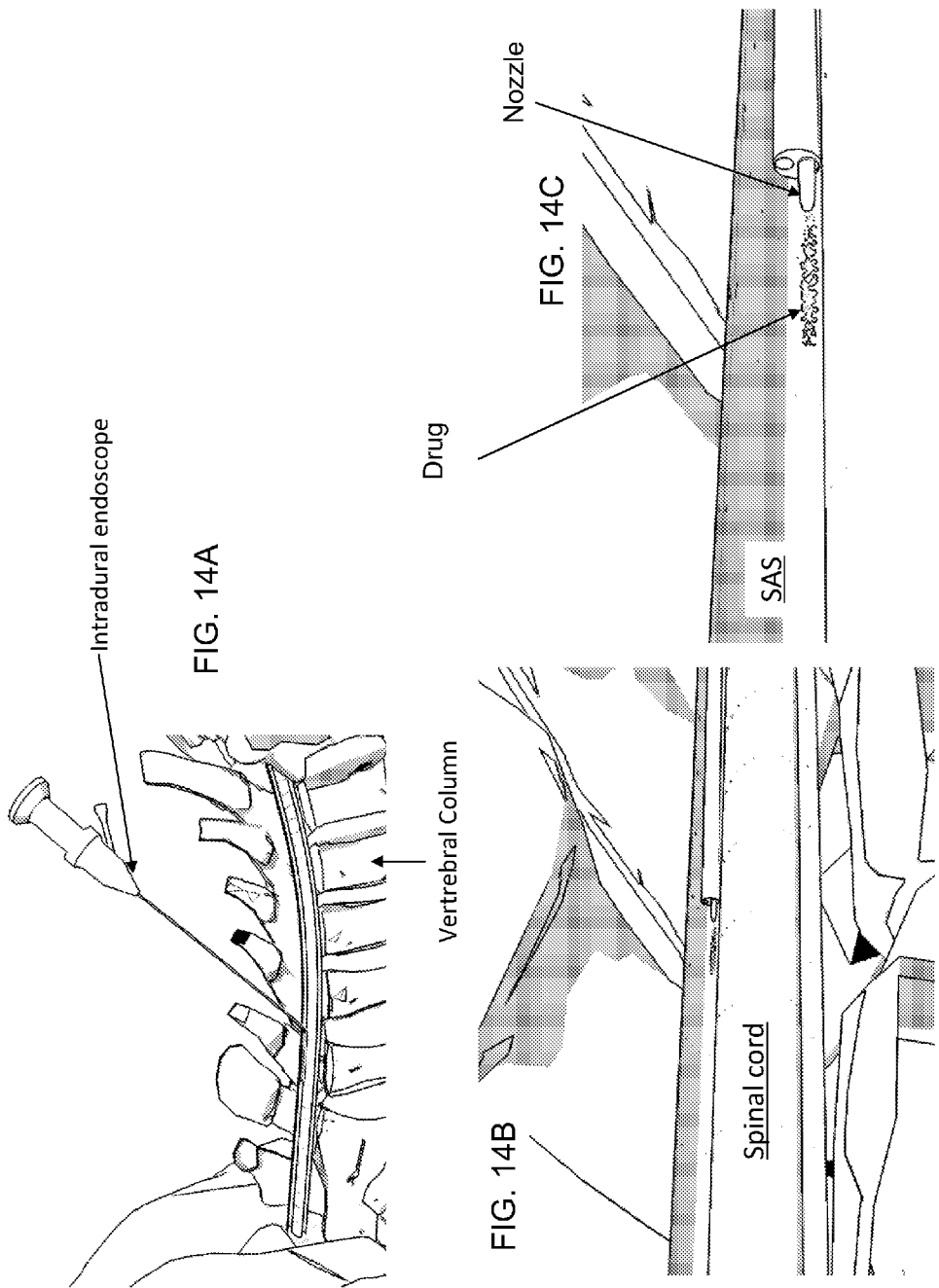

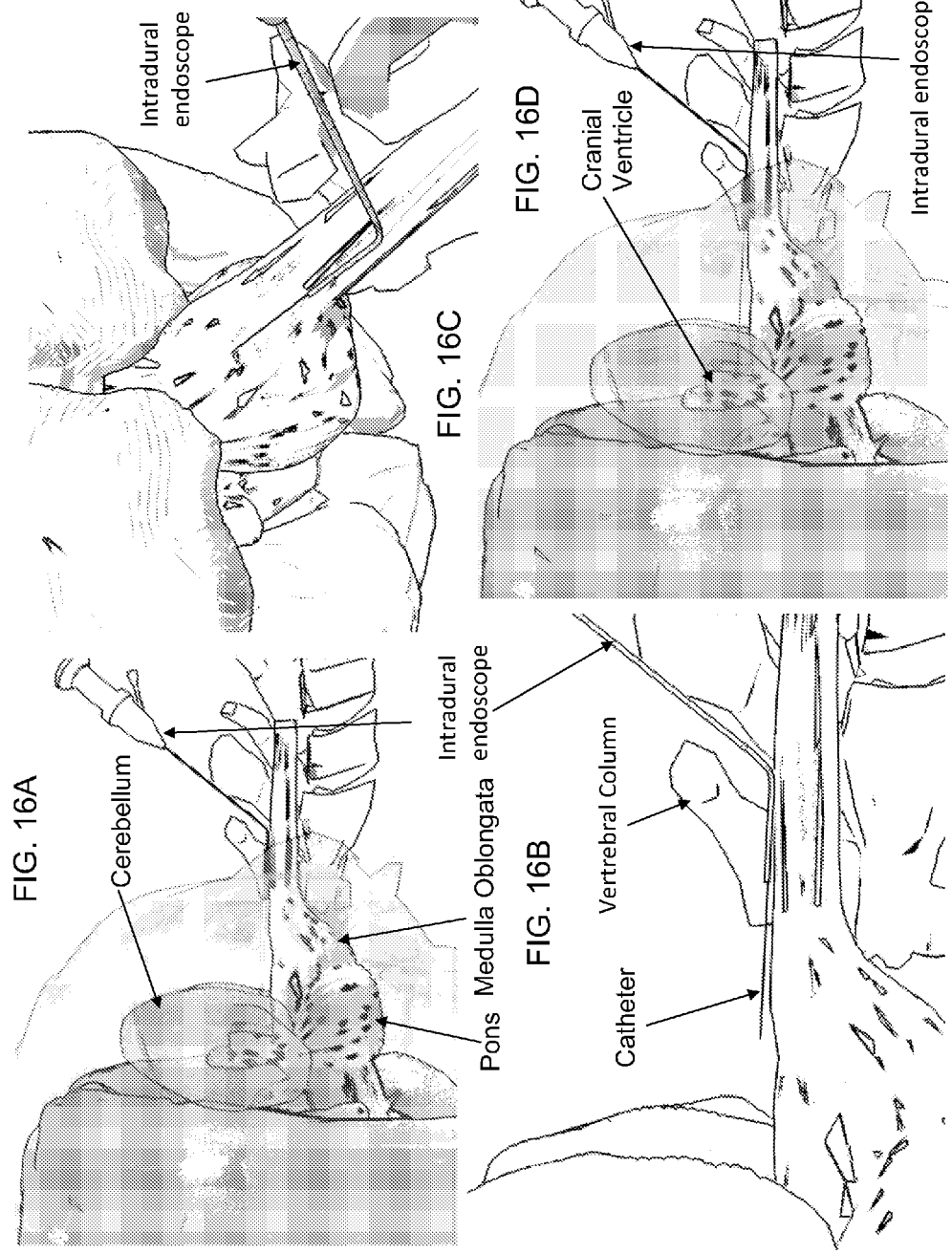

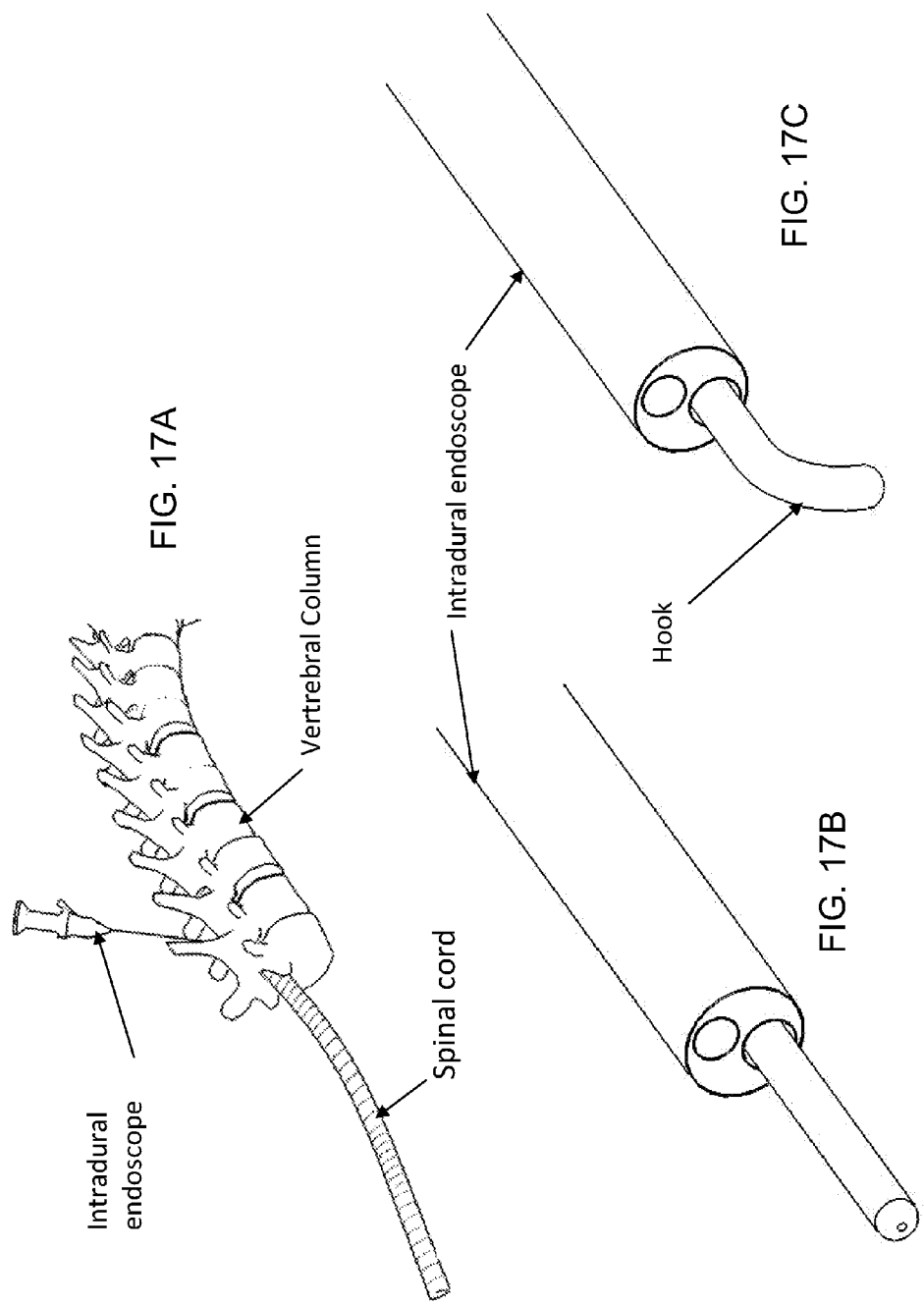

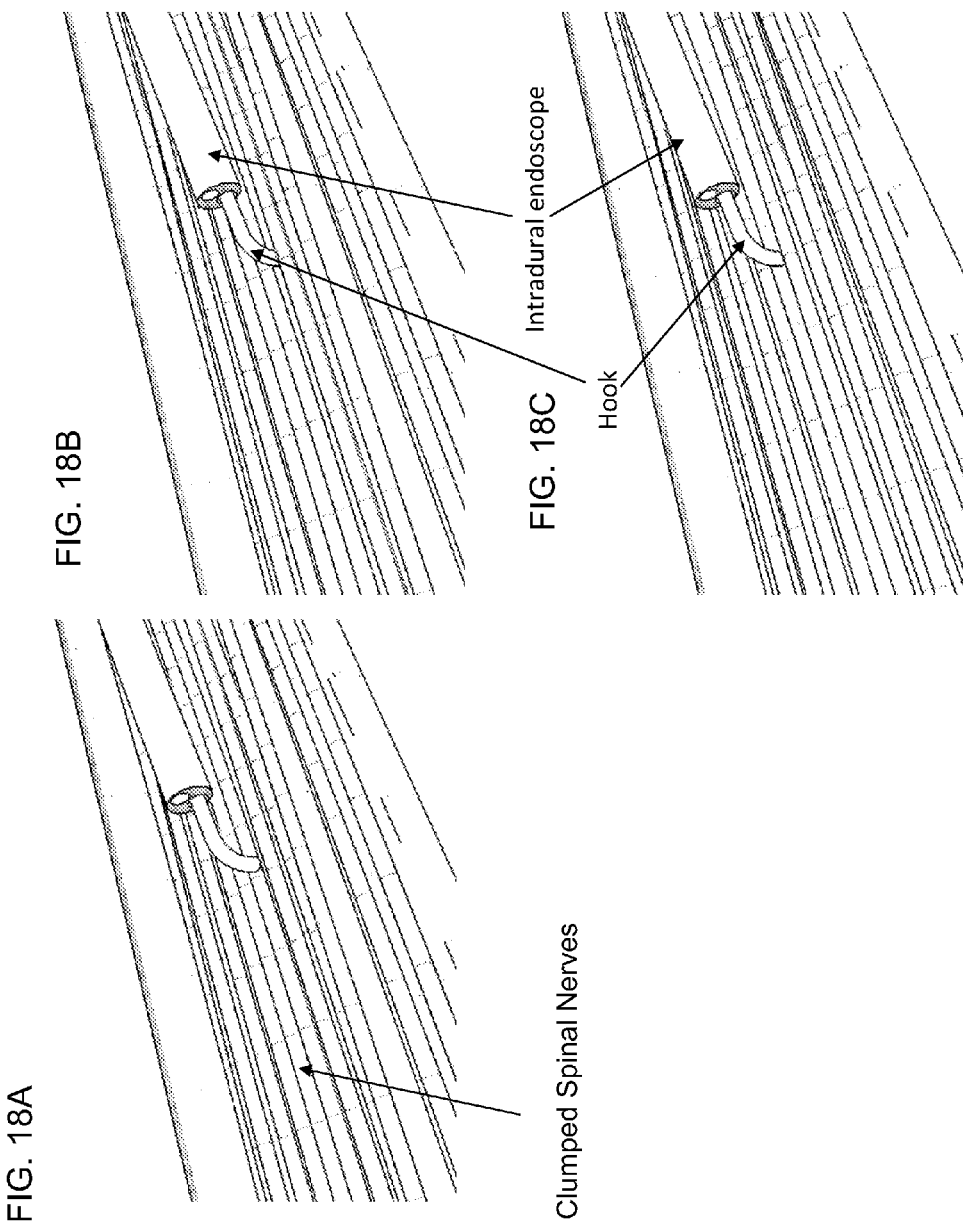

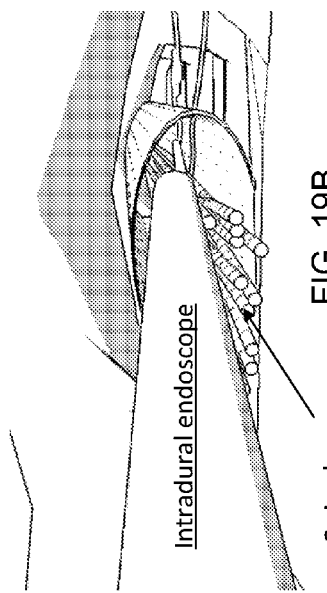
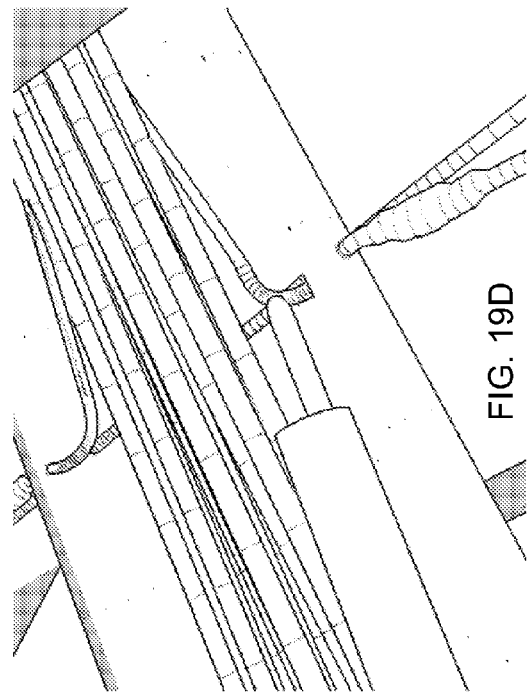
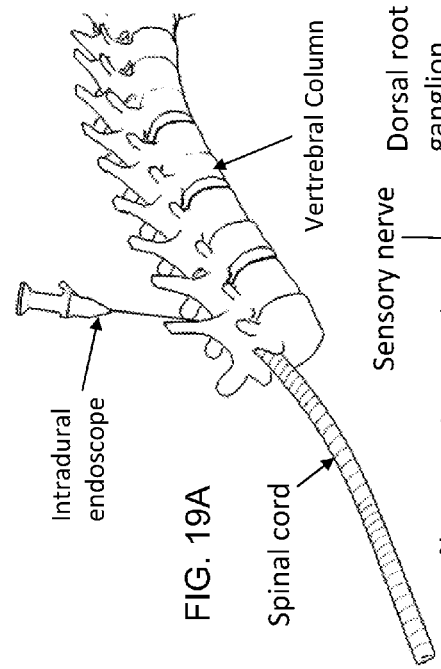
FIG. 19A  FIG. 19B  FIG. 19C  FIG. 19D

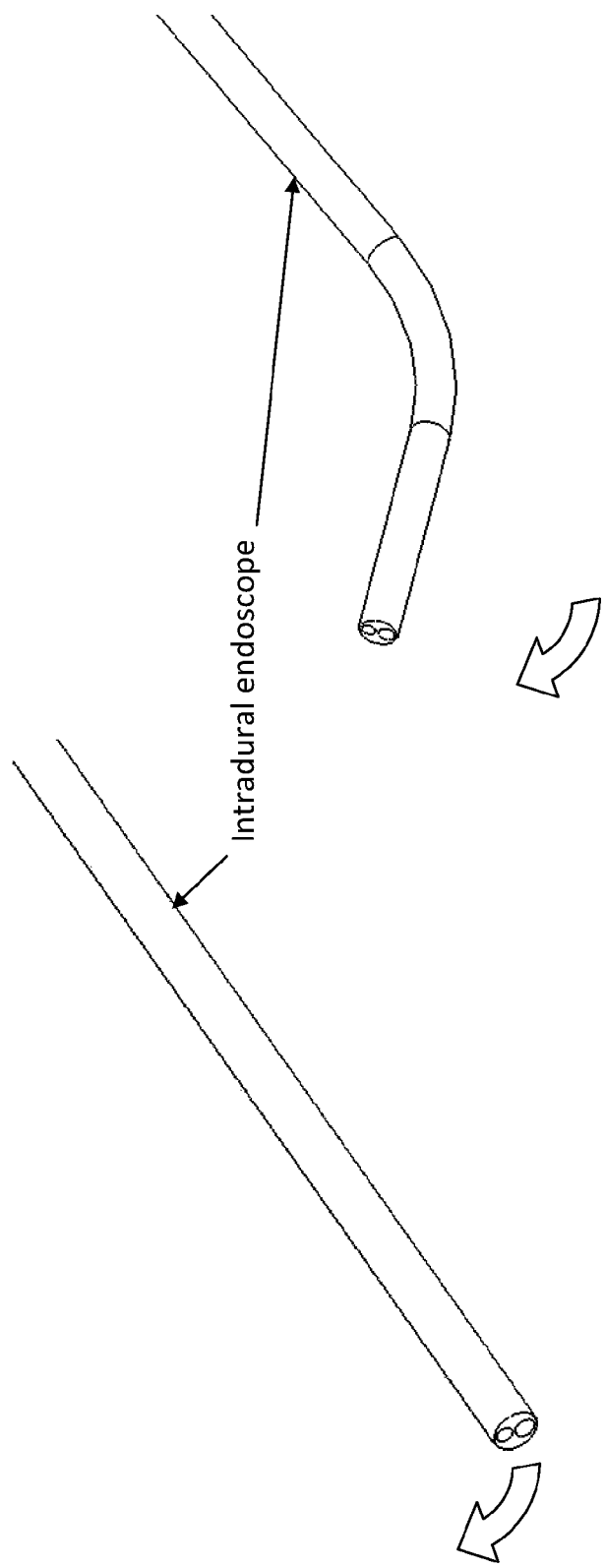

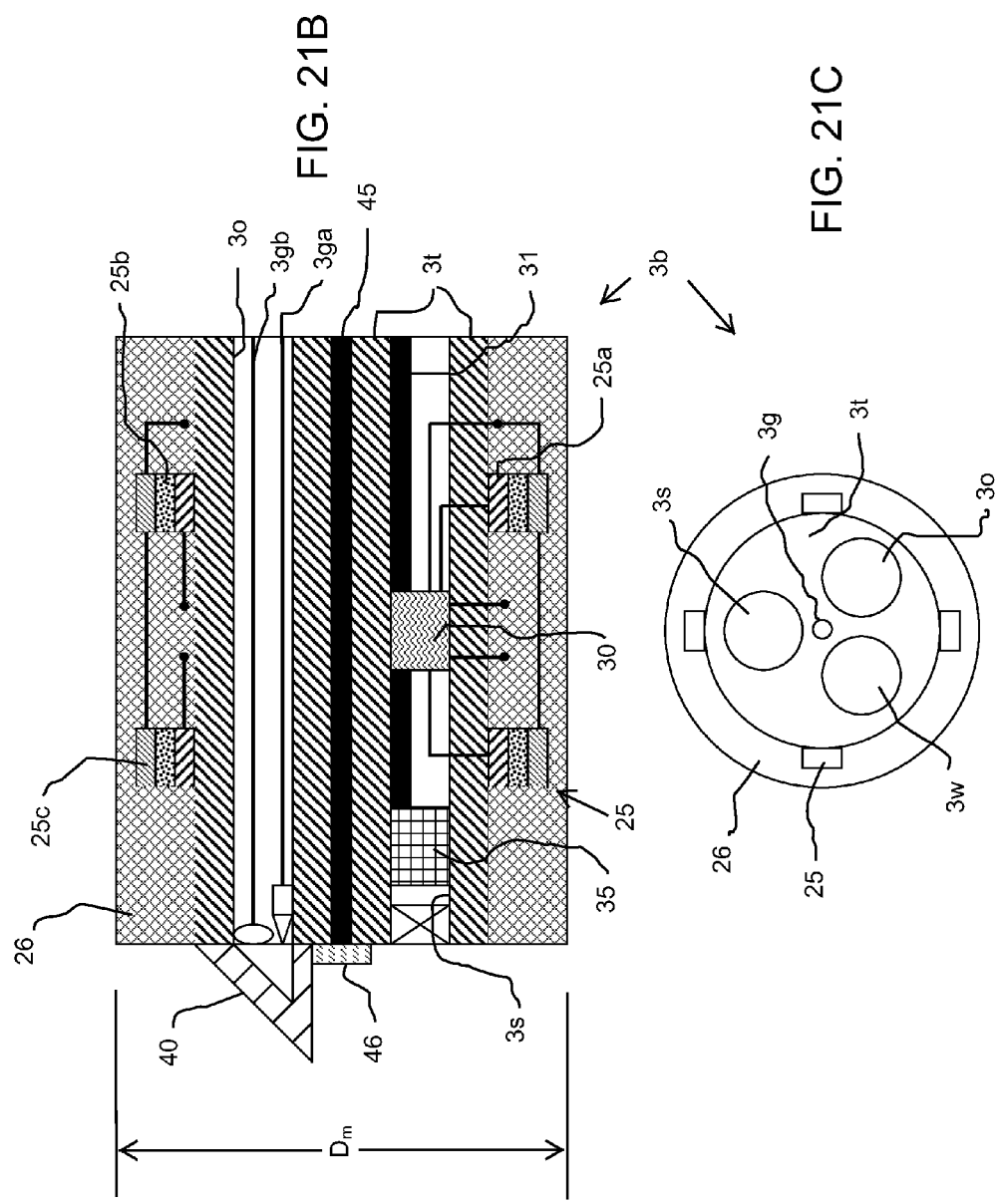

INTRADURAL ENDOSCOPE

CROSS-REFERENCE TO RELATED APPLICATIONS

This application claims benefit of U.S. Provisional Patent Application Ser. Nos. 61/261,136, filed Nov. 13, 2009, and 61/319,664, filed Mar. 31, 2010, which are herein incorporated by reference in their entireties.

BACKGROUND OF THE INVENTION

Field of the Invention

The present invention generally relates to apparatus and methods for an intradural endoscope.

Description of the Related Art

During the 20th century, brain neurosurgery has advanced via the introduction of microsurgical techniques, the development of new tools such as aneurysm clips, and the description of new operative approaches. Surgeons have developed elegant mechanisms to remove parts of the bones making up the skull (craniotomy) and operate on structures deep within the brain while attempting to minimize complications relating to the approach. Furthermore, the surgical approach to the intracranial and spinal subarachnoid space has historically consisted of the skin incision, dissection to either the cranium or spinal bony covering, removal of some bone, and dissection through the meninges to gain access to the neurological structures.

During the last 20 years, the development of endovascular neurosurgery has resulted in the creation of specialized devices for application within arteries. These devices include not only catheters and guidewires, but also embolic materials that can be introduced via catheters, thereby enabling the enhancement of some procedures that are performed via craniotomy following embolization, and thereby eliminating the need for craniotomy altogether in other cases. However, these techniques have heretofore been limited to the intravascular space (i.e., the space within blood vessels) because that was seen as the only available route of access for catheterization of the intracranial contents.

SUMMARY OF THE INVENTION

The present invention provides apparatuses and methods for an intradural endoscope. In one embodiment, a method for treating a patient, includes inserting an endoscope into an intradural space of the patient via an interspace of a vertebral column of the patient; steering the endoscope along the intradural space to a location; and performing a medical procedure at the location using a working lumen of the endoscope.

In another embodiment, a steerable endoscope system for treatment of a patient includes an endoscope. The endoscope includes a tube having a guide portion, an optical lumen, a working lumen, and a maximum outer diameter less than or equal to 3.5 mm. The endoscope further includes a head having a port for access to the working lumen. The system further includes a steering actuator operable to move the guide portion between a straight position and a curved position; a steering system in communication with the steering actuator and operable to steer the guide portion; and a video interface for receiving an object image from the optical lumen.

BRIEF DESCRIPTION OF THE DRAWINGS

FIGS. 1A-C illustrate insertion of an endoscope into a cervical interspace of the vertebral column of a patient, according to one embodiment of the present invention.

FIGS. 2A-C illustrate advancement of the endoscope into the spinal subarachnoid space (SAS).

FIG. 3A illustrates histology of the SAS. FIG. 3B illustrates advancement of the endoscope into the spinal SAS. FIG. 3C illustrates advancement of the endoscope into the intracranial SAS.

FIGS. 4A and 4B illustrate advancement of the endoscope into the spinal SAS. FIGS. 4C and 4D illustrate advancement of the endoscope into the intracranial SAS.

FIGS. 5A-E illustrate insertion of an endoscope into a lumbar interspace of the vertebral column of a patient, according to another embodiment of the present invention.

FIGS. 6A and 6B illustrate a medical procedure, such as ablation, being performed using the intradural endoscope, according to another embodiment of the present invention.

FIGS. 7A-8C illustrate another medical procedure, such as a brain tumor biopsy or resection, being performed using the intradural endoscope, according to another embodiment of the present invention.

FIGS. 9A-9D illustrate another medical procedure, such as a spinal cord tumor biopsy or resection, being performed using the intradural endoscope, according to another embodiment of the present invention.

FIGS. 10A and 10B illustrate another medical procedure, such as a spinal cord syrinx (syringomyelia) or brainstem syrinx (syringobulbia) drainage, being performed using the intradural endoscope, according to another embodiment of the present invention.

FIGS. 11A-11C illustrate another medical procedure, such as implantation of an electrode assembly in the spinal SAS, being performed using the intradural endoscope, according to another embodiment of the present invention.

FIGS. 13A-13C illustrate another medical procedure, such as implantation of an electrode assembly to modulate a dorsal root, being performed using the intradural endoscope, according to another embodiment of the present invention.

FIGS. 14A-14C illustrate another medical procedure, such as drug injection into the spinal SAS, being performed using the intradural endoscope, according to another embodiment of the present invention.

FIGS. 16A-16D illustrate another medical procedure, such as a ventriculostomy, being performed using the intradural endoscope, according to another embodiment of the present invention.

FIGS. 17A-18C illustrate another medical procedure, such as intradural dehiscence, being performed using the intradural endoscope, according to another embodiment of the present invention.

FIGS. 19A-19D illustrate another medical procedure, such as spinal modulation, being performed using the intradural endoscope, according to another embodiment of the present invention.

FIGS. 20A and 20B illustrate steering of the endoscope.

FIGS. 21A-C illustrate a steerable endoscope system, according to another embodiment of the present invention.

DETAILED DESCRIPTION OF THE INVENTION

The detailed description that follows is not to be taken in a limiting sense, but is made primarily for the purpose of illustrating the general principles of the various aspects of the present invention. The scope of the invention is best defined by the claims appended hereto.

FIGS. 1A-C illustrate insertion of an endoscope into a cervical interspace of the vertebral column of a patient, according to one embodiment of the present invention. FIGS. 2A-C illustrate advancement of the endoscope into the spinal subarachnoid space (SAS). FIG. 3B illustrates advancement of the endoscope into the spinal SAS. FIG. 3C illustrates advancement of the endoscope into the intracranial SAS. FIGS. 4A and 4B illustrate advancement of the endoscope into the spinal SAS. FIGS. 4C and 4D illustrate advancement of the endoscope into the intracranial SAS. A spinal needle (not shown) may be inserted through the skin and the dural membrane (or dura mater) via one of the cervical interspaces C3-4 into the spinal SAS by a surgeon or robot (not shown). The endoscope tube may then be inserted through a lumen of the spinal needle and into the spinal SAS by the surgeon or robot. As a tip of the endoscope tube exits the spinal needle, the endoscope tip may be steered by the robot or surgeon along the spinal SAS. Steering of the endoscope tube may be visually monitored using an optical lumen of the endoscope. The endoscope tube may be steered along the SAS toward a head of the patient until arriving in a location in the spinal or intracranial SAS to perform a medical procedure (discussed below).

Alternatively, a trocar (not shown) may be inserted instead of the spinal needle into the SAS by the robot or surgeon. The trocar may carry a cannula (not shown). The cannula may then be inserted into the SAS over the trocar and attached to the skin, such as by a suture. The endoscope may then be inserted into the SAS through a lumen of the trocar and steered along the trocar by the surgeon or robot.

Alternatively, after introducing the spinal needle into the SAS, the surgeon or robot (not shown) may insert a guidewire (not shown) through the needle lumen and along the SAS. The needle may be removed and the surgeon or robot may dilate the tract created by the needle by inserting one or more dilators (not shown) over the guidewire. Instead of or in addition to the dilators, the surgeon or robot may insert a sheath into the needle tract over the guidewire and along the SAS. The sheath may then be attached to the skin, such as by a suture. The endoscope may then be inserted through a lumen of the sheath and along the SAS by passing over the guidewire.

Alternatively, the endoscope may be introduced into the spinal SAS via any of the vertebral column interspaces, such as the thoracic or lumbar interspaces.

Figure 2D:
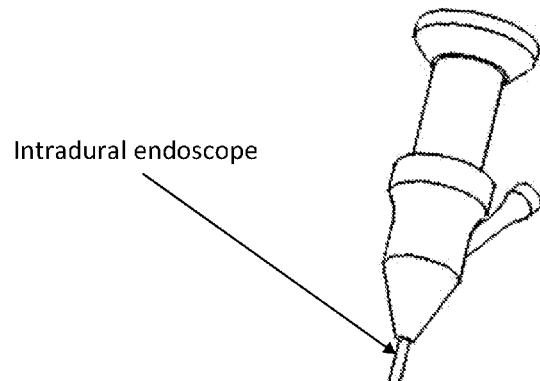
FIG. 2D illustrates histology of the SAS.
Figure 2C:
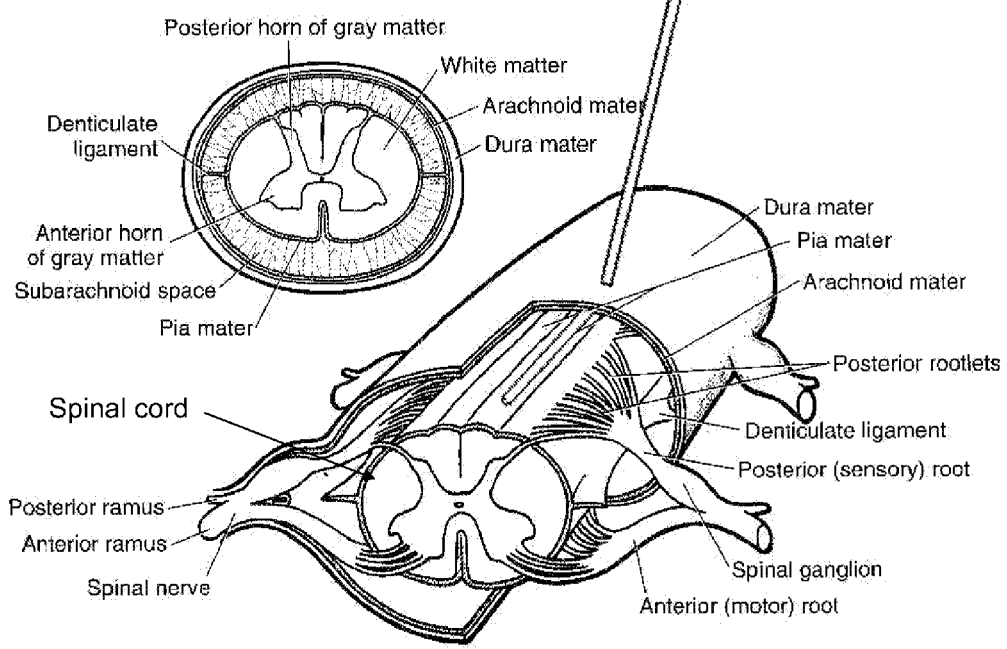
Figure 8C:
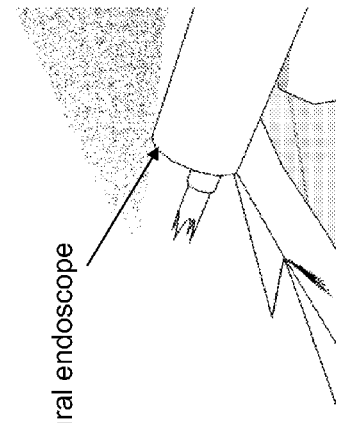
Figure 8B:
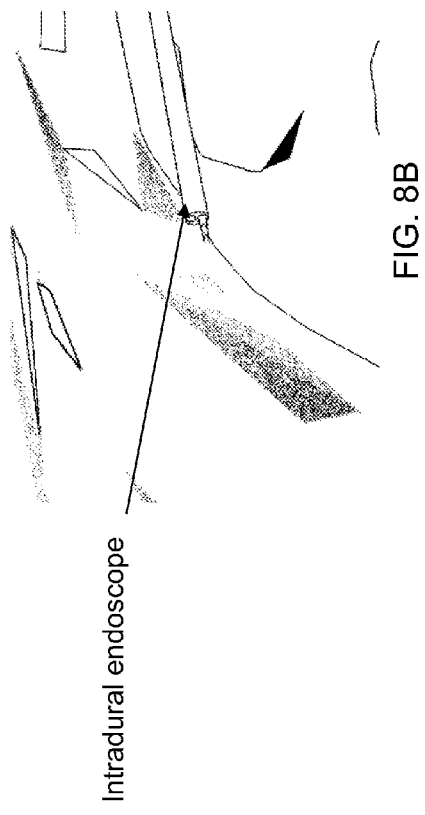
Figure 8A:

FIGS. 2D and 3A illustrate histology of the SAS. The SAS is a compartment that contains the body of the spinal cord and cerebrospinal fluid (CSF) which fills and surrounds the ventricles (cavities) of the brain and the spinal cord, and acts as a lubricant and a mechanical barrier against shock. The SAS is defined between the arachnoid mater and the pia mater. The intracranial SAS is the SAS located above the foramen magnum, and the spinal SAS is the SAS located below the foramen magnum, though the spaces are contiguous without a physical barrier between them.

Alternatively, due to trauma or death, other intradural spaces may be created, such as a subdural space, and the intradural endoscope may be inserted into any intradural space to treat a patient or study a cadaver.

FIGS. 5A-E illustrate insertion of an endoscope into a lumbar interspace of the vertebral column of a patient, according to another embodiment of the present invention. A spinal needle (not shown), or any of the above-discussed alternatives, may be inserted through the skin and the dural membrane via one of the lumbar interspaces L3-4 into the spinal SAS by a surgeon or robot (not shown). The endoscope tube may then be inserted through a lumen of the spinal needle and into the spinal SAS by the surgeon or robot. As a tip of the endoscope tube exits the spinal needle, the endoscope tip may be steered by the robot or surgeon along the spinal SAS. Steering of the endoscope tube may be visually monitored using the optical lumen of the endoscope. The endoscope tube may be steered along the SAS toward a head of the patient until placed in a location in the spinal or intracranial SAS to perform a medical procedure (discussed below).

In another embodiment (not shown), the dural membrane may be closed after the medical procedure is complete. In order to close the dural membrane, a dural closer (not shown) may be coupled to the cannula or sheath. The dural closer may be operable to close the dural membrane as the sheath or cannula is withdrawn from the spinal SAS. The dural closer may include a needle, or other suture-delivering apparatus, that is actuated by the surgeon or robot to deliver a suture through the dura. Alternatively, the dural closer may be operated by the surgeon or robot to inject a sealant, such as a biocompatible polymer, into the dura opening created by the needle. Alternatively, the dural closer may be operated by the surgeon or robot to set a plug in the dural opening. Alternatively, the dural closer may be any device discussed and/or illustrated in U.S. Pat. App. Pub. Nos. 2009/0230168, 2008/0287923, 2009/0005793, and 2008/0319475, which are herein incorporated by reference in their entireties.

FIGS. 6A and 6B illustrate a medical procedure, such as ablation, being performed using the intradural endoscope, according to another embodiment of the present invention. Ablation may be used to treat patients with neck or back pain from facet joint problems due to arthritis or injury. Nerves that go directly to the individual facet joints may be targeted. Ablation may also be used treat patients with complex regional pain syndrome involving arms or legs by interrupting the sympathetic nerve supply to the involved arm or leg. Ablation may also be used to treat pain from degenerative disks, occipital neuralgia and certain types of abdominal pain.

A laser or optical waveguide for delivering an output of a laser external to the patient may be disposed in and/or extend from a working lumen of the endoscope. Once the endoscope has been steered to a desired location in the spinal SAS, such as a targeted nerve, the laser may be operated to ablate the targeted nerve, thereby semi-permanently blocking or numbing the nerve. Proper location of the targeted nerve may be verified by monitoring the endoscope using the lens/fiber optic system (FOS). Alternatively, the ablation may be performed using an electrically active needle heated by passing a radio-frequency current through the needle or by injecting a cryothermal fluid through a nozzle coupled to an end of the endoscope and in fluid communication with the working lumen. Alternatively, the laser may be inserted through the working lumen after the endoscope is positioned at the desired location.

Alternatively, the desired location may be in the intracranial SAS and the laser may be operated to create lesions in the brain to treat chronic pain syndrome or Parkinson's disease.

FIGS. 7A-8C illustrate another medical procedure, such as a brain tumor biopsy or resection, being performed using the intradural endoscope, according to another embodiment of the present invention. Once the endoscope has been steered to a desired location in the intracranial SAS, such as the brainstem, a portion of an aspirator may be inserted through a working lumen of the endoscope. The aspirator may include a pump, a catheter, and a needle. The pump may be located externally of the patient and in fluid communication with the needle via the catheter. The pump may be a syringe or an electric vacuum pump. The needle and a portion of the catheter may be inserted through the working lumen and visualized by the lens/FOS as the needle exits the working lumen. The needle may then be advanced by the surgeon or robot to puncture an exterior surface of the tumor. The pump may then be operated to aspirate a sample for biopsy, a substantial portion of the tumor, or an entirety of the tumor. The tumor may be a brainstem glioma.

FIGS. 9A-9D illustrate another medical procedure, such as a spinal cord tumor biopsy or resection, being performed using the intradural endoscope, according to another embodiment of the present invention. Once the endoscope has been steered to a desired location in the spinal SAS, such as the brainstem, a portion of an aspirator may be inserted through a working lumen of the endoscope. The aspirator may include a pump (not shown), a catheter, and a needle. The pump may be located externally of the patient and in fluid communication with the needle via the catheter. The pump may be a syringe or an electric vacuum pump. The needle and a portion of the catheter may be inserted through the working lumen and visualized by the lens/FOS as the needle exits the working lumen. The needle may then be advanced by the surgeon or robot to puncture an exterior surface of the tumor. The pump may then be operated to aspirate a sample for biopsy, a substantial portion of the tumor, or an entirety of the tumor. Alternatively, any of the tumors discussed above may be ablated.

FIGS. 10A and 10B illustrate another medical procedure, such as a spinal cord syrinx (syringomyelia) or brainstem syrinx (syringobulbia) drainage, being performed using the intradural endoscope, according to another embodiment of the present invention. Once the endoscope has been steered to a desired location in the spinal SAS or intracranial SAS, such as to the syrinx, the aspirator may be used to puncture and drain the syrinx. The needle may not be required to puncture the syrinx. Alternatively, a shunt (not shown) may be implanted in the syrinx. The shunt may include a catheter and a check valve. The catheter may extend from the syrinx to an abdominal cavity, such as the peritoneal cavity and the check valve may operate to allow fluid flow from the syrinx to the abdominal cavity and prevent fluid flow from the abdominal cavity to the syrinx. Alternatively, the shunt catheter may extend to the right atrium, pleural cavity, or gallbladder.

FIGS. 11A-11C illustrate another medical procedure, such as implantation of an electrode assembly in the spinal SAS, being performed using the intradural endoscope, according to another embodiment of the present invention. Once the endoscope has been steered to a desired location in the spinal SAS, such as at one or more pre-selected segments of the spinal cord, the electrode assembly may be inserted through the working lumen and into the spinal SAS. The electrode assembly may be implanted in electrical communication, such as proximate to or in contact with one or more target nerves. Once implanted, the electrodes may be used to modulate one or more target nerves, such as to treat one or more medical conditions discussed above for ablation. To modulate the nerves, the electrode assembly may be implanted in one of the dorsal sulci.

Figure 12A:
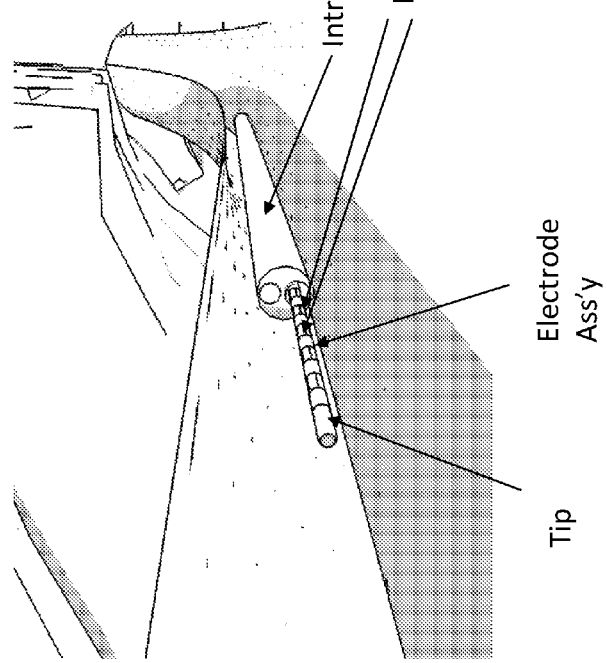
FIGS. 12A and 12B illustrate a neuromodulator.
Figure 12B:
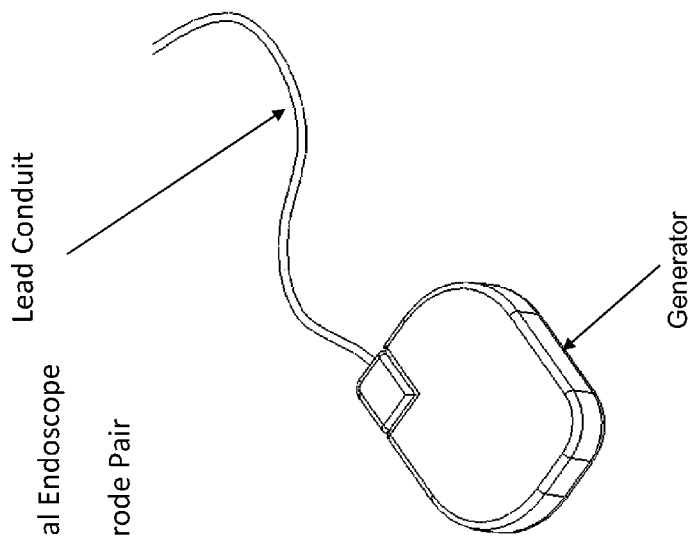

FIGS. 12A and 12B illustrate a neuromodulator. The electrode assembly may be part of the neuromodulator. The electrode assembly may be a catheter electrode. The catheter electrode may include an elongated lead conduit having proximal and distal ends and a tip at the distal end of the lead conduit. The lead conduit may include an elongated tubular construction section having a lumen. The lead conduit may be flexible. The lead conduit may be made from a biocompatible material, such as a nylon tube surrounded by braided stainless steel with a polyurethane coating. The tip may include a short section of flexible tubing having a lumen.

One or more pairs of electrodes may be disposed along a length of the tip. The electrodes may be rings made from an electrically conductive and biocompatible material, such as a metal or alloy. An outer diameter of the electrodes may be about the same as the outer diameter of the tip so that the electrodes form a smooth, continuous outer surface with the outer surface of the tip tubing. Lead wires may be attached to a respective electrode and extend through the lumen of the lead conduit to a generator. Each lead wire may be attached to a respective electrode. A distal end of the tip may be rounded to form a guide nose. The lead conduit may receive an end of the tip and the lead conduit and the tip may be connected, such as with adhesive.

The neuromodulator may further include the generator. The generator may be implanted in the patient's body, such as in a pocket formed by the implanting surgeon just below the skin in the abdomen. The generator may be in electrical communication with the pairs of electrodes via lead wires housed in the lead conduit. The generator may be operable to deliver a signal to the target nerves, thereby inhibiting or blocking pain.

The generator may include a housing, a microprocessor controller, a battery, an inverter or pulser, an antenna, and a transceiver. The housing may be sealed and made from a biocompatible material, such as titanium. The controller may operate the inverter or pulser to deliver the output signal according to predetermined instructions. The controller may be reprogrammed by wireless communication with an external computer (not shown) via the antenna and receiver. The generator may further include a battery charger operable to generate electricity from wireless signals and recharge the battery. Alternatively, the generator may be worn by the patient externally and the lead conduit may extend percutaneously to the implanted electrodes. Alternatively, the generator may include only a housing, an antenna, a receiver, and an RF generator and deliver the signal to the electrodes when powered wirelessly, analogously to a passive RFID tag. The inverter or pulser may supply the signal to the electrodes and may supply a pulse or sinusoidal wave. A voltage, frequency, and/or current of the signal may be varied.

Alternatively, one or more pairs of electrodes may be used as sensors so that the modulator controller may detect natural activity along the target nerves. The controller may modulate the target nerve in response to detected activity, such as that indicative of pain.

Alternatively, the electrode assembly may be implanted on a surface of the brain or within brain tissue and used to detect and/or treat epilepsy.

FIGS. 13A-13C illustrate another medical procedure, such as implantation of an electrode assembly to modulate a dorsal root, being performed using the intradural endoscope, according to another embodiment of the present invention. Once the endoscope has been steered to a desired location in the spinal SAS, such as in visual communication with a dorsal root of the spinal cord, the electrode assembly may be inserted through the working lumen and into the spinal SAS. The lens/FOP may be used to monitor implantation of the electrode assembly in electrical communication with the dorsal root by the robot or surgeon. Specifically, the electrode assembly may be implanted in electrical communication with the ganglion of the dorsal root, such as proximate to or in contact with the dorsal root ganglion. Once implanted, the electrodes may be used to modulate the dorsal root ganglion, such as to treat one or more medical conditions discussed above for ablation.

FIGS. 14A-14C illustrate another medical procedure, such as drug injection into the spinal SAS, being performed using the intradural endoscope, according to another embodiment of the present invention. Once the endoscope has been steered to a desired location in the spinal SAS, one or more drugs may be injected through a working lumen of the endoscope and into the spinal SAS via a nozzle connected to the distal end of the endoscope. A check valve may also be disposed in the working lumen at or near the distal end to allow drug flow from the working lumen and into the spinal SAS and prevent flow of CSF into the working lumen. A pump (i.e., syringe or electric pump) may be connected to the working lumen to inject the drugs. The drugs may be anesthetics, chemotherapeutics, or corticosteroids. Alternatively, stem cells may be injected.

FIGS. 15A-15D illustrate another medical procedure, such surgical clipping of a cerebral aneurysm, being performed using the intradural endoscope, according to another embodiment of the present invention. Once the endoscope has been steered to a desired location in the intracranial SAS, such as in view of the aneurysm, a clip may be inserted through the working lumen of the endoscope using a catheter. The clip may be operably coupled to the catheter via an actuator holding the clip in an open position. A wire may extend from the actuator and through a lumen of the catheter. The catheter may be used to position the open clip over a neck of the aneurysm by the surgeon or robot using the endoscope to view the procedure. Once the open clip is in the position, the surgeon or robot may exert tension in the wire. The clip may abut a shoulder of the catheter while the actuator is pulled longitudinally along the catheter by the wire, thereby releasing the clip and allowing the clip to engage the aneurysm neck while moving to the closed position. The clip may be made from a biocompatible material, such as a metal or alloy. Alternatively, the endoscope may be used to assist an endovascular coiling operation.

Figure 15A:
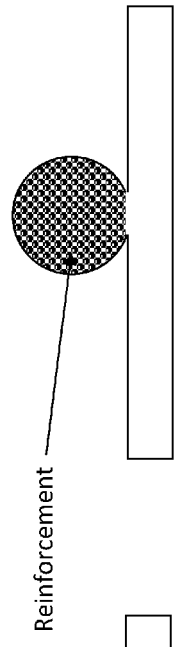
FIGS. 15A-15D illustrate another medical procedure, such surgical clipping of a cerebral aneurysm, being performed using the intradural endoscope, according to another embodiment of the present invention.
Figure 15E:
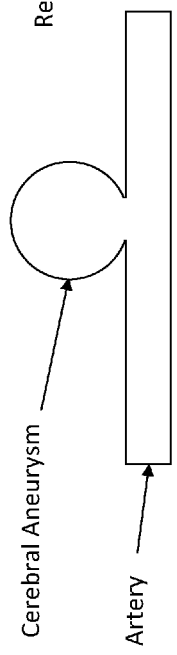
FIG. 15E illustrates a cerebral aneurysm reinforced using the intradural endoscope, according to another embodiment of the present invention.
Figures 15B, 15C:
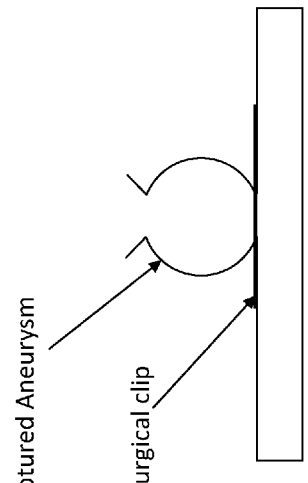
Figure 15D:
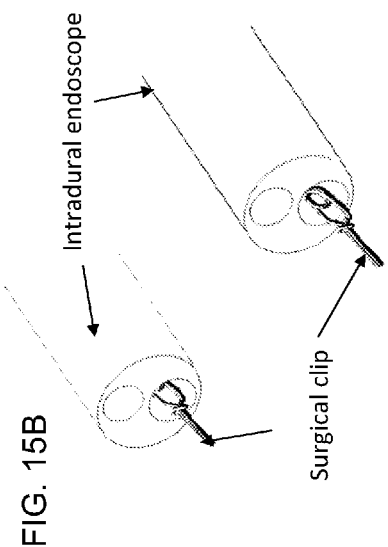

FIG. 15E illustrates a cerebral aneurysm reinforced using the intradural endoscope, according to another embodiment of the present invention. If the aneurysm is detected before rupture, a reinforcement fluid may be injected into the aneurysm through the working lumen of the endoscope. The reinforcement fluid may be a cement or polymer. The fluid may cure by hydration or by application of UV light to the fluid using the endoscope.

FIGS. 16A-16D illustrate another medical procedure, such as a ventriculostomy, being performed using the intradural endoscope, according to another embodiment of the present invention. Once the endoscope has been steered to a desired location in the intracranial SAS, such as to a cranial ventricle, a needle may be inserted through the working lumen. The needle may be inserted by being connected to a catheter or rod. Using the endoscope for visual guidance, the surgeon or robot may puncture a floor of the cranial ventricle with the needle, thereby creating a opening allowing drainage of CSF to basal cisterns and relieving excess pressure due to blockage of the ventricular system caused by hydrocephalus, intraventricular hematoma, or intraventricular tumor. The opening may be formed in a floor of the third ventricle. Alternatively, a shunt (not shown) may be implanted in the cerebral ventricle. The shunt may include a catheter and a check valve or flow control valve. The catheter may extend from the ventricle to an abdominal cavity, such as the peritoneal cavity and the check valve may operate to allow fluid flow from the ventricle to the abdominal cavity and prevent fluid flow from the abdominal cavity to the ventricle. Alternatively, the shunt catheter may extend to the right atrium, pleural cavity, or gallbladder. Alternatively, a stent (not shown) may be implanted into the cerebral aqueduct.

FIGS. 17A-18C illustrate another medical procedure, such as intradural dehiscence, being performed using the intradural endoscope, according to another embodiment of the present invention. Once the endoscope has been steered to a desired location in the spinal SAS, such as in view of a clump of adhered spinal nerves (arachnoiditis), a hook may be inserted through the working lumen of the endoscope using a catheter or rod. The hook may be connected to a distal end of the catheter or rod. Alternatively, the hook may be housed in the working lumen in a retracted position and then extended using a mechanical, hydraulic, or electrical actuator.

The hook may be made from a ductile biocompatible material, such as a metal or alloy, such as stainless steel or titanium. The hook may have a permanent bend and be elastically deformed when inserted into the working lumen so that the hook returns to the curved shape upon extension from the working lumen. Alternatively, the hook may be made from a shape memory material, such as a metal, alloy, or polymer or an electroactive polymer. The hook may then be operable between a straight position for transportation through the working lumen and a curved position for deployment from the working lumen. The hook may be moved from the straight to the curved position by sending a signal via electrical leads or a cable extending through the catheter or working lumen. If the material is shape memory, the signal may be sent to an actuator operably coupled to the hook. The actuator may heat the hook or expose the hook to a magnetic field, thereby operating the hook. If the material is electroactive, the signal may be sent directly to the hook.

Once extended and shaped, the endoscope may be steered by the surgeon or robot to insert the hook between two adhered nerves. The endoscope may then be moved along the adhered nerves, thereby dragging or pushing the hook between the nerves and separating the nerves. The operation may be repeated until all of the nerves in the clump are separated.

FIGS. 19A-19D illustrate another medical procedure, such as spinal modulation, being performed using the intradural endoscope, according to another embodiment of the present invention. A radio frequency (RF) probe may be connected to a distal end of the endoscope and lead wires may extend to an external generator similar or identical to the neuromodulator generator, discussed above. The endoscope may be steered to a location so that the probe is in electrical communication, such as in contact or close proximity to a first spinal nerve in the SAS. The nerve may be modulated, i.e., stimulated or blocked, to determine if the nerve is a target nerve causing a condition, as discussed above for ablation. The endoscope may then be steered to a second nerve and the operation repeated until the target nerve is determined. The target nerve may then be treated, as discussed above.

Another medical procedure (not shown) which may be performed using the intradural endoscope may be performed using the intradural endoscope having dual working lumens. CSF from the SAS may be circulated through a first of the working lumens to an external heat exchanger for adding or removing heat to the CSF. A pump may receive fluid from the heat exchanger and discharge the heated/cooled CSF into the second of the working lumens, thereby returning the CSF to the patient.

FIGS. 20A and 20B illustrate steering of the endoscope. A tip of the endoscope may be steered by the surgeon or robot between a straight position and a curved position. The endoscope tip may be steered by a steering actuator, such as an electroactive polymer actuator, one or more steering wires, or by a magnetic field (discussed below).

Figure 21A:
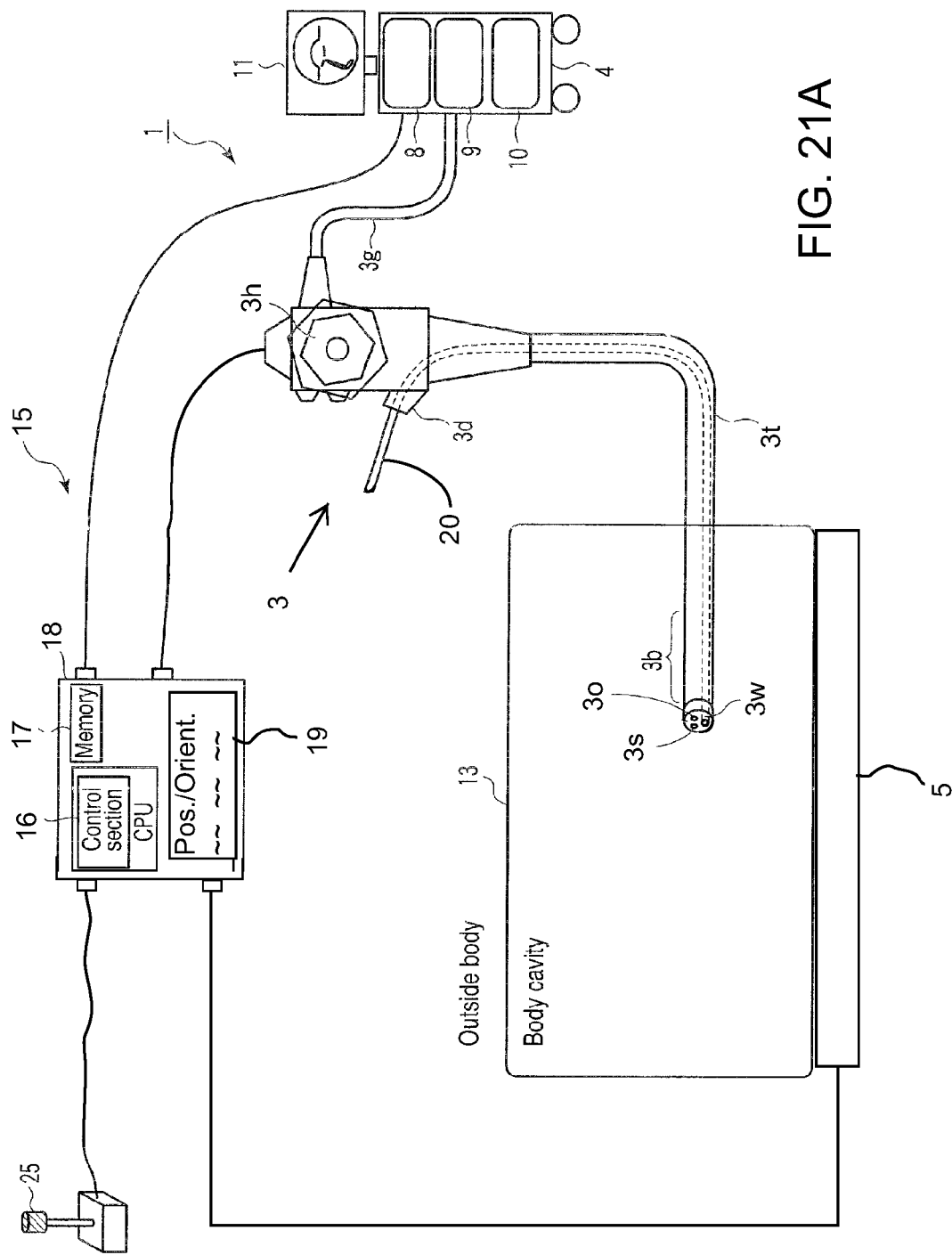

FIGS. 21A-C illustrates a steerable endoscope system 1, according to another embodiment of the present invention. The steerable endoscope system 1 may be used to perform any of the medical procedures, discussed above and illustrated in FIGS. 1-19. The system 1 may include an endoscope 3, a video interface 4, and a steering system 15. Alternatively, the video interface 4 and steering system 15 may be consolidated into one unit.

The endoscope 3 may include a head 3h having a bore for receiving an optical cable 3g or housing an electronics package, such as a video processor, and a side port 3d for access to a working lumen 3w. The interface 4 may include a light source 9 or the endoscope may have an internal light source. The endoscope 3 may further include the tube 3t having two or more lumens 3s,3o,3w,3g (i.e., concentric or eccentric) connected to the head 3h. The optical lumen 3o may house the optics or video electronics and the working lumen 3w may conduct fluid or a medical device 20 (discussed above). The endoscope 3 may be analog and/or digital. The optical lumen 3o may house an optical fiber bundle 3ga for conducting light from an external light source 9 or an internal light source, such as one or more LEDs, to illuminate the object. The optical lumen 3o may further house a second fiber bundle 3gb or lens and image sensor (i.e., CCD or CMOS) for capturing and/or conducting the object image to an eyepiece or video processor 8. The second fiber bundle 3gb or image sensor may deliver the image or signal indicative of the image to an analog front end (AFE) 10 and the AFE 10 may digitize the signal and send the signal to the video processor 8 via an electrical cable or optical fiber/cable. The video processor 8 may output the image to a monitor 11 for viewing by the surgeon.

The endoscope tube 3t may be made from a biocompatible material, such as a polymer, metal, or alloy. To be suitable for travel within the SAS, a maximum outer diameter $D_m$ of the tube 3t (including thickness of a barrier layer 26, discussed below) may be less than or equal to three and a half millimeters, three millimeters, two and a half millimeters, two millimeters, one and a half millimeters, or one millimeter. The endoscope tube 3t may include a guide portion, such as a tip 3b, that includes a plurality of electroactive polymer (EAP) actuators 25 disposed along a length thereof. Each actuator 25 may be in electrical communication with a tip controller 30 via leads. The tip controller 30 may selectively operate each actuator by supplying a power signal thereto. Based upon the signal received from the tip controller 30, the respective actuator 25 may change the shape of the guide portion 3b.

Each EAP actuator 25 may include an active member portion 25a made from an EAP material, a counter-electrode portion 25c and a region including an electrolyte 25b disposed between the active member portion and the counter-electrode portion. An outer surface of the tube 3t may serve as a substrate layer. The actuator 25 may further include a barrier layer 26, with the active member portion, counter-electrode portion and the electrolyte region disposed between the substrate layer and barrier layer. The EAP may be one or more of polyaniline, polypyrrole, polysulfone and polyacetylene. If the tube material is electrically conductive, an insulating layer may be disposed between the active portion 25a and the tubing outer surface.

One or more actuators 25 may be disposed around the tube outer surface at relative axes thereof. In this manner, operation of the actuators 25 along a first axis may steer the tip about a first axis and operation of the actuators along a second axis may steer the tip about a second axis. Two actuators 25 may be opposing along the same axis so that a first actuator may be extended and a second actuator may be contracted, thereby operating the actuator pairs in tandem. Similarly, steering may be accomplished off-axis by operating an actuator or pair along first and second axes simultaneously.

The steering system 15 may include a computer 18, such as a personal computer or laptop, having a microprocessor 16, memory 17, a monitor 19, and a controller, such as a joystick 25. The steering system 15 may provide power to and be in data communication with the tip controller 30 via an electrical cable 31 extending through the steering lumen 3s. The power signal may be DC and data communication may be via AC signals multiplexed with the power signal. The surgeon may steer the tip 3b by operating the joystick 25. The microprocessor 16 may translate the joystick movements into discrete commands and send the commands to the tip controller 30. The tip controller 30 may then selectively operate one or more of the actuators 25 based on the commands, thereby steering the tip 3b. The cable 31 may also be used to deliver power to and transfer the object image from the image sensor.

The guide portion 3b may further include one or more feedback sensors 35. The feedback sensors 35 may include a tracking device, such as a sensing coil, and the steering system may further include one or more electromagnetic field generators 5 located adjacent the patient 13. The electromagnetic field generators 5 may be operated to generate magnetic fields at different respective frequencies. The electromagnetic fields may cause alternating voltage drops at respective frequencies across the sensing coil indicative of three-dimensional position and two-dimensional orientation. Rotational orientation of the guide portion about its longitudinal axis may be measured by adding a second transponder, by a rotation sensor of a robot (discussed below), or neglected. The tip controller 30 may measure the voltage drops at the different frequencies and may also measure phases of the voltage drops. The tip controller 30 may report the data to the computer 18. Additionally or alternatively, the feedback sensors 35 may include one or more strain gages, such as two, each oriented along a transverse axis, to ensure that the actuators are functioning properly and/or the tip is not obstructed from steering. The sensors 35 may be in power and data communication with the tip controller via leads.

Alternatively, the tracking device may be the tip 3b made from a magnetic material or have a magnetic tag housed therein and the steering system 15 may further include a magnetic scanner operable to detect the magnetic tip/tag in three dimensional space and to generate position data of the magnetic tip/tag. Alternatively, the tracking device may be the tip 3b made from a radio-opaque material or have a radio-opaque tag housed therein and the steering system 15 may further include an fluoroscopic scanner operable to detect the radio-opaque tip/tag in three dimensional space and to generate position data of the magnetic tip/tag.

Additionally, the guide portion 3b may include one or more biosensors (not shown) disposed along an outer surface thereof and in communication with the CSF in the SAS. The biosensors may include one or more of a pH sensor, a voltage meter, a temperature sensor, a pressure sensor, and an electroencephalograph (EEG).

The endoscope tube 3t may further include a guide lumen 3g formed centrally therethrough and a guidewire 45 disposed through the guide lumen. The guidewire 45 may reinforce the tube, thereby providing increased stiffness thereto. The guidewire 45 may be longitudinally coupled to the tube 3t via a cap 46. Once the endoscope tip 3b has been steered to the desired location in the SAS and a procedure performed, the endoscope tube 3t may be removed without having to remove the guidewire 45. Leaving the guidewire 45 in place allows subsequent medical procedures to be performed with catheters or non-steerable endoscopes since they may be run-in over the guidewire. Additionally or alternatively to the guidewire 45, the tip 3b may be stiffened by operating all of the actuators 25 in tension simultaneously.

The endoscope tip 3b may further include a nose 40 to guide the tube through the SAS. The nose 40 may be made from a transparent and biocompatible material, such as glass, laminated glass, or a polymer, such as polycarbonate or acrylic. The nose 40 may be quarter-ellipsoid or quarer-spherical in shape. The nose 40 may be coupled to the tip 3b, the guidewire 45, or both. The nose 40 may be coupled to the tip 3b, such as by bonding using an adhesive.

Additionally, the steering system 15 may include a robot to articulate the tube 3t, for example, advancing the tube into the patient 13. The steering system 15 may include a second controller, such as a joystick, so that the surgeon may control advancement or retraction of the tube with one joystick and steer the tip 3b with the other joystick. The steering system 15 may further include a depth sensor for monitoring the length of the tube 3t inserted into the patient 13. The steering microprocessor 16 may display the position data received from the transponder and the biodata received from the biosensors in real-time for viewing by the surgeon so that the surgeon may make steering decisions including whether or not to advance or even retrieve the endoscope.

Alternatively, the control signals from the steering system 15 may correspond to a surgeon selectable shape for the guide portion 3b stored in the memory 17. Alternatively, the control signals from the steering system 15 may be generated by a shape-generating algorithm based on medical diagnostic imaging data.

Additionally, the guide portion 3b may include a lead module and a plurality of following modules. When each following module reaches a position previously occupied by the lead module, the actuators 25 may cause the following module to replicate the orientation that the lead module had when it was at that particular position. Lead module orientation data and position data may be provided by the sensors 35. Additionally, the EAP actuators 25 may be controlled to provide a desired curvature to the guide catheter portion at each of a plurality of loci along the length of the guide portion, such as "S" shaped, in-plane and out-of-plane curves as well as more complex, curvatures. Alternatively, the following modules may be unactuated and possess sufficient flexibility to follow the path.

Alternatively, the tip 3b may be made separately from the rest of the tube 3t and connected thereto, such as by adhesive. Alternatively, instead of disposing the actuators 25 along or around an outer surface of the tip 3b, the tip 3b may be made from a composite material and the actuators 25 may be formed integrally with the tip 3b as the tip 3b is being made. Alternatively, the actuators 25 may be formed on a substrate and the substrate may then be connected to the tip 3b. Alternatively, the actuators may be disposed or formed along or around an inner surface of the tip 3b.

Alternatively, the sensors 35 and tip controller 30 may be omitted. The tip 3b may instead include filters, such as diodes, that allow the microprocessor to selectively operate the actuators at different threshold voltages. The threshold voltages may be positive or negative. Alternatively, one or more actuators 25 may only be disposed on one axis and the cable 31 may be directly connected to the actuators 25, thereby obviating the need for the controller 30. Alternatively, the endoscope lumens may be concentric and include the actuators on only one axis. In this alternative, a swivel and motor may be assembled as part of a tube assembly, thereby allowing the motor to rotate a distal portion of the tube (relative to the head) relative to a proximate portion of the tube, thereby achieving similar control to having actuators on two axes.

Alternatively, the optical lumen 3o may be split into two sub-lumens: one sub-lumen for the light source and one sub-lumen for the image.

A suitable EAP guide portion is further discussed and illustrated in U.S. Pat. App. Pub. No. 2004/0143160, which is herein incorporated by reference in its entirety.

Figure 22:
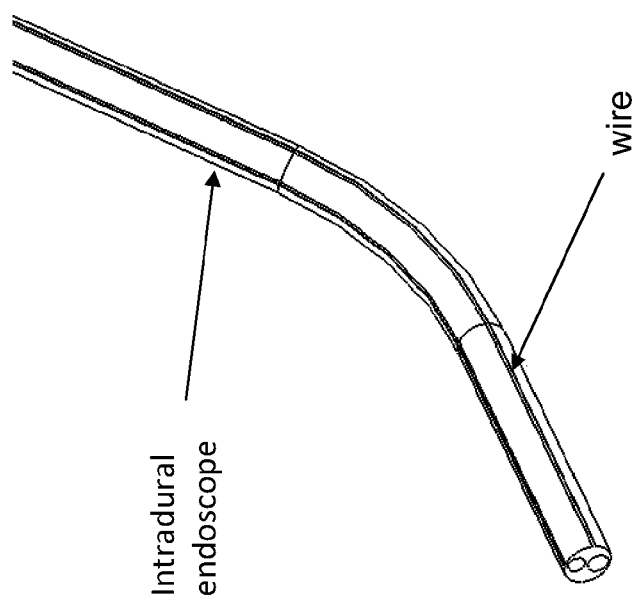
FIG. 22 illustrates a wire steerable endoscope, according to another embodiment of the present invention.

FIG. 22 illustrates a wire steerable endoscope, according to another embodiment of the present invention. The wire steerable endoscope may be used to perform any of the medical procedures, discussed above and illustrated in FIGS. 1-19. The endoscope tube portion may further include one or more steering lumens. Each steering lumen may house a wire connected eccentrically to a distal end of the endoscope tube. Selectively pulling a respective wire bends an end toward a longitudinal axis of the wire.

Figure 23:
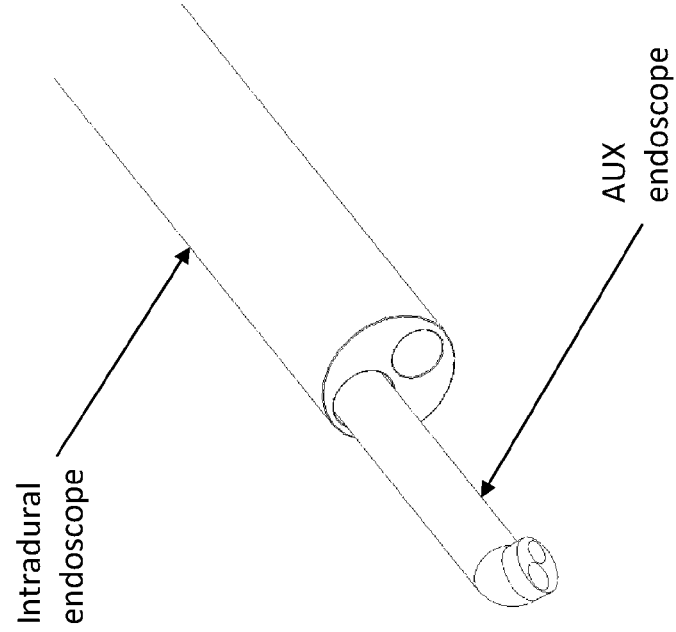
FIG. 23 illustrates deployment of an auxiliary endoscope through the working lumen of the intradural endoscope, according to another embodiment of the present invention.

FIG. 23 illustrates deployment of an auxiliary endoscope through the working lumen of the intradural endoscope, according to another embodiment of the present invention. Deployment of the auxiliary endoscope may be used to facilitate any of the medical procedures, discussed above and illustrated in FIGS. 1-19. In order to allow passage through the working lumen, the auxiliary endoscope may include only an optical lumen and a simplified actuation system similar to that of the hook, discussed above, so that the tip may be straight for insertion through the working lumen and curved after exit from the working lumen. The tube of the auxiliary endoscope may then be rotated to provide peripheral visualization relative to the intradural endoscope.

Alternatively, a guide portion of the endoscope may be made from a magnetic material and steered by varying a magnetic field created externally of the patient as discussed and illustrated in U.S. Pat. App. Pub. No. 2003/0125752, which is herein incorporated by reference in its entirety

What is claimed is:

1. A method for treating a patient, comprising:
   inserting an endoscope tube into an intradural space of the patient via an interspace of a vertebral column of the patient, wherein the endoscope tube has an electroactive tip, a guide portion containing one or more actuators, and a maximum outer diameter of less than 2.5 mm;
   steering the endoscope tube along the intradural space to a location by causing the electroactive tip to bend via an electrical signal directly supplied to the electroactive tip and along an electrical cable extending along a steering lumen of the endoscope tube and a steering system in communication with the electrical cable while visually monitoring the steering using an optical lumen of the endoscope tube and a video monitor in communication with the optical lumen, wherein the steering system comprises:
      a computer having a microprocessor, a memory, a monitor, a first controller and a second controller, wherein the microprocessor translates movements from the first controller into commands and sends the commands to a tip controller to operate the one or more actuators, and wherein the microprocessor translates movements from the second controller into commands to advance or retract the endoscope tube;
   once the endoscope tube has been steered to the location, inserting a medical device through a working lumen of the endoscope tube; and
   performing a medical procedure at the location using the medical device while visually monitoring the medical procedure using the optical lumen and the video monitor.

2. The method of claim 1, wherein the intradural space is a spinal subarachnoid space.

3. The method of claim 1, wherein:
   the endoscope tube is inserted through a cannula or sheath, and
   the method further comprises operating a dural closer while removing the cannula or sheath.

4. The method of claim 1, wherein:
   the endoscope tube is inserted through a cannula or sheath, and
   the method further comprises operating a dural puncture element while positioning the cannula or sheath.

5. The method of claim 1, wherein the medical procedure is implantation of electrodes.

6. The method of claim 1, wherein the medical procedure is diagnostic or therapeutic neuromodulation.

7. The method of claim 1, wherein:
   the endoscope tube carries a guidewire in a guide lumen thereof, and
   the method further comprises removing the endoscope tube from the intradural space and leaving the guidewire in place.

8. The method of claim 1, further comprising deploying an auxiliary endoscope through the working lumen before insertion of the medical device or after removal of the medical device from the working lumen.

9. The method of claim 1, wherein the interspace is a cervical interspace.

10. The method of claim 2, wherein the endoscope tube is steered along the spinal subarachnoid space into an intracranial subarachnoid space.

11. The method of claim 1, wherein the maximum outer diameter of the tube is less than or equal to 1 mm.

12. The method of claim 1, wherein the steering system comprises
   a robot operable to articulate the tube.

13. The method of claim 1, wherein:
   the electroactive tip has a tracking device in communication with the steering system, and
   the steering system displays a position of the electroactive tip.

14. The method of claim 1, wherein:
   the electroactive tip has one or more biosensors in communication with the steering system, and
   the steering system displays data from the biosensors.

15. The method of claim 1, wherein:
   the electroactive tip has a strain gage in communication with the steering system, and
   the steering system displays an orientation of the electroactive tip.

* * * * *